(12) United States Patent
Del Curto

(10) Patent No.: US 7,846,427 B2
(45) Date of Patent: Dec. 7, 2010

(54) STABILIZED INTERFERON LIQUID FORMULATIONS

(75) Inventor: Maria Dorly Del Curto, Corvino San Quicico (IT)

(73) Assignee: Ares Trading S.A., Aubonne (CH)

( * ) Notice: Subject to any disclaimer, the term of this patent is extended or adjusted under 35 U.S.C. 154(b) by 1195 days.

(21) Appl. No.: 10/582,027

(22) PCT Filed: Dec. 10, 2004

(86) PCT No.: PCT/EP2004/053407

§ 371 (c)(1), (2), (4) Date: Jun. 8, 2006

(87) PCT Pub. No.: WO2005/058346

PCT Pub. Date: Jun. 30, 2005

(65) Prior Publication Data

US 2007/0104682 A1    May 10, 2007

(30) Foreign Application Priority Data

Dec. 11, 2003  (EP)  ................... 03104646
Jul. 13, 2004  (EP)  ................... 04103349

(51) Int. Cl.
*A61K 38/21*   (2006.01)
*A61K 38/00*   (2006.01)
*C07K 14/565*  (2006.01)

(52) U.S. Cl. .................. 424/85.6; 530/351; 514/12

(58) Field of Classification Search ................ None
See application file for complete search history.

(56) References Cited

U.S. PATENT DOCUMENTS

| | | | | |
|---|---|---|---|---|
| 5,814,485 | A * | 9/1998 | Dorin et al. | 435/69.51 |
| 5,858,001 | A * | 1/1999 | Tsals et al. | 604/135 |
| 5,997,856 | A | 12/1999 | Hora et al. | |
| 6,569,420 | B2 * | 5/2003 | Chen et al. | 424/85.4 |
| 6,582,728 | B1 | 6/2003 | Platz et al. | |
| 2002/0172661 | A1 * | 11/2002 | Shirley et al. | 424/85.6 |
| 2007/0059285 | A1 | 3/2007 | Samaritani et al. | |
| 2007/0248674 | A1 | 10/2007 | Del Curto et al. | |

2007/0292391 A1  12/2007  Samaritani et al.

FOREIGN PATENT DOCUMENTS

| | | |
|---|---|---|
| WO | WO 90/03784 A1 | 4/1990 |
| WO | WO 03/002152 A2 | 1/2003 |
| WO | WO 2005/117949 A1 | 12/2005 |

OTHER PUBLICATIONS

Hultgren, C. et al. "The Antiviral Compound Ribavirin Modulates the T Helper (Th) 1/Th2 Subset Balance in Hepatitis B and C Virus-Specific Immune Responses", *Journal of General Virology*, 1998, pp. 2381-2391, vol. 79.
Mark, D. F. et al. "Site-Specific Mutagenesis of the Human Fibroblast Interferon Gene", *Proc. Natl. Acad. Sci. USA*, Sep. 1984, pp. 5662-5666, vol. 81.
Rubinstein, S. et al. "Convenient Assay for Interferons", *Journal of Virology*, Feb. 1981, pp. 755-758, vol. 37, No. 2.
Brewster, M. E. et al. "Use of 2-Hydroxypropyl-β-cyclodextrin as a Solubilizing and Stabilizing Excipient for Protein Drugs", *Pharmaceutical Research*, 1991, pp. 792-795, vol. 8, No. 6.
Arakawa, T. et al. "Factors affecting short-term and long-term stabilities of proteins" *Advanced Drug Delivery Reviews*, 2001, pp. 307-326, vol. 46, Nos. 1-3.
Irie, T. et al. "Cyclodextrins in peptide and protein delivery" *Advanced Drug Delivery Reviews*, 1999, pp. 101-123, vol. 36.
U.S. Appl. No. 11/597,987 (claims only), filed Nov. 30, 2006 (not yet published), pp. 1-4.

* cited by examiner

*Primary Examiner*—Robert Landsman
*Assistant Examiner*—Bruce D Hissong
(74) *Attorney, Agent, or Firm*—Saliwanchik, Lloyd & Saliwanchik

(57) ABSTRACT

Stabilized liquid pharmaceutical composition comprising an interferon (IFN) or an isoform, mutein, fused protein, functional derivative, active fraction or salt thereof, wherein said formulation is a solution that comprises a buffer, a cyclodextrin, an isotonicity agent and an anti-oxidant are described here. Preferably the interferon is interferon beta-1a and the cyclodextrin is HPBCD. These formulations are stable at room temperature, thus bringing the advantage of lower costs for formulation storage and increased safety for the patient with respect to possible "errors" during handling. As a matter of fact, having such formulations stable at room temperature reduces the risk of formation of degradation products potentially responsible for adverse events (e.g. immunogenicity).

35 Claims, 12 Drawing Sheets

Pre-melting secondary structure content:

|  | 190-260 nm | 195-260 nm | 200-260 nm | 205-260 nm | 210-260 nm |
|---|---|---|---|---|---|
| Helix | 37,88% | 45,33% | 47,95% | 48,63% | 47,78% |
| Antiparallel | 5,95% | 4,78% | 5,30% | 5,28% | 5,28% |
| Parallel | 7,73% | 6,28% | 5,85% | 5,73% | 6,03% |
| Beta-Turn | 16,33% | 14,80% | 14,45% | 14,50% | 14,50% |
| Rndm. Coil | 29,55% | 24,18% | 24,18% | 24,08% | 24,80% |

Post-melting secondary structure content:

|  | 190-260 nm | 195-260 nm | 200-260 nm | 205-260 nm | 210-260 nm |
|---|---|---|---|---|---|
| Helix | 33,58% | 39,38% | 41,18% | 41,98% | 41,03% |
| Antiparallel | 8,95% | 6,58% | 6,58% | 6,28% | 6,45% |
| Parallel | 8,45% | 7,28% | 7,28% | 6,95% | 7,13% |
| Beta-Turn | 17,15% | 15,75% | 15,75% | 15,38% | 15,58% |
| Rndm. Coil | 31,40% | 28,40% | 28,40% | 27,70% | 28,43% |

Pre-melting secondary structure content:

| | 190-260 nm | 195-260 nm | 200-260 nm | 205-260 nm | 210-260 nm |
|---|---|---|---|---|---|
| Helix | 32,87% | 41,13% | 42,97% | 42,83% | 42,27% |
| Antiparallel | 8,90% | 5,70% | 6,13% | 6,10% | 6,20% |
| Parallel | 8,83% | 7,10% | 6,73% | 6,73% | 6,90% |
| Beta-Turn | 17,20% | 15,37% | 15,13% | 15,23% | 15,30% |
| Rndm. Coil | 33,23% | 28,57% | 27,20% | 27,23% | 27,63% |

Post-melting secondary structure content:

| | 190-260 nm | 195-260 nm | 200-260 nm | 205-260 nm | 210-260 nm |
|---|---|---|---|---|---|
| Helix | 30,03% | 37,40% | 39,03% | 39,10% | 38,37% |
| Antiparallel | 11,93% | 7,07% | 7,00% | 6,73% | 7,00% |
| Parallel | 9,37% | 7,77% | 7,50% | 7,53% | 7,60% |
| Beta-Turn | 17,83% | 16,03% | 15,83% | 15,77% | 15,93% |
| Rndm. Coil | 34,37% | 30,30% | 29,27% | 29,47% | 29,90% |

| Pre-melting secondary structure content: | | | | | |
|---|---|---|---|---|---|
| | 190-260 nm | 195-260 nm | 200-260 nm | 205-260 nm | 210-260 nm |
| Helix | 25,50% | 30,30% | 35,00% | 30,50% | 28,70% |
| Antiparallel | 21,70% | 11,40% | 8,70% | 8,80% | 9,80% |
| Parallel | 9,80% | 9,20% | 8,40% | 9,90% | 10,00% |
| Beta-Turn | 19,30% | 17,60% | 17,20% | 17,50% | 17,90% |
| Rndm. Coil | 33,70% | 32,60% | 30,00% | 34,80% | 36,30% |
| Post-melting secondary structure content: | | | | | |
| | 190-260 nm | 195-260 nm | 200-260 nm | 205-260 nm | 210-260 nm |
| Helix | 24,20% | 25,60% | 28,80% | 21,70% | 20,70% |
| Antiparallel | 18,70% | 13,20% | 10,30% | 11,50% | 13,20% |
| Parallel | 11,20% | 11,50% | 10,70% | 13,60% | 12,80% |
| Beta-Turn | 18,80% | 18,20% | 18,00% | 19,10% | 19,80% |
| Rndm. Coil | 40,50% | 40,80% | 37,40% | 43,00% | 43,40% | pH 5.1

page 1 …

```
                            SEQUENCE LISTING

<160> NUMBER OF SEQ ID NOS: 2

<210> SEQ ID NO 1
<211> LENGTH: 3
<212> TYPE: PRT
<213> ORGANISM: Artificial sequence
<220> FEATURE:
<223> OTHER INFORMATION: Linker peptide

<400> SEQUENCE: 1

Glu Phe Met
1

<210> SEQ ID NO 2
<211> LENGTH: 13
<212> TYPE: PRT
<213> ORGANISM: Artificial sequence
<220> FEATURE:
<223> OTHER INFORMATION: Linker peptide

<400> SEQUENCE: 2

Glu Phe Gly Ala Gly Leu Val Leu Gly Gly Gln Phe Met
1               5                   10
```

STABILIZED INTERFERON LIQUID FORMULATIONS

CROSS-REFERENCE TO RELATED APPLICATION

This application is the U.S. national stage application of International Patent Application No. PCT/EP2004/053407, filed Dec. 10, 2004, the disclosure of which is hereby incorporated by reference in its entirety, including all figures, tables and amino acid or nucleic acid sequences.

FIELD OF THE INVENTION

The invention relates generally to stabilized liquid pharmaceutical composition comprising an interferon (IFN) or an isoform, mutein, fused protein, functional derivative, active fraction or salt thereof, wherein said formulation is a solution that comprises a buffer, a cyclodextrin, an isotonicity agent and an anti-oxidant and use thereof.

BACKGROUND OF THE INVENTION

Interferons are cytokines, i.e. soluble proteins that transmit messages between cells and play an essential role in the immune system by helping to destroy microorganisms that cause infection and repairing any resulting damage. Interferons are naturally secreted by infected cells and were first identified in 1957. Their name is derived from the fact that they "interfere" with viral replication and production.

Interferons exhibit both antiviral and antiproliferative activity. On the basis of biochemical and immunological properties, the naturally-occurring human interferons are grouped into three major classes: Interferon-alpha (leukocyte), Interferon-beta (fibroblast) and interferon-gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non-specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential anti-tumor and antiviral activities.

The three major IFNs are referred to as IFN-α, IFN-β and IFN-γ. Such main kinds of IFNs were initially classified according to their cells of origin (leukocyte, fibroblast or T cell). However, it became clear that several types might be produced by one cell. Hence leukocyte IFN is now called IFN-α, fibroblast IFN is IFN-β and T cell IFN is IFN-γ. There is also a fourth type of IFN, lymphoblastoid IFN, produced in the "Namalwa" cell line (derived from Burkit's lymphoma), which seems to produce a mixture of both leukocyte and fibroblast IFN.

The interferon unit or international unit for interferon (U or IU, for international unit) has been reported as a measure of IFN activity defined as the amount necessary to protect 50% of the cells against viral damage. The assay that may be used to measure bioactivity is the cytopathic effect inhibition assay as described (Rubinstein, et al. 1981; Familletti, P. C., et al., 1981). In this antiviral assay for interferon about 1 unit/ml of interferon is the quantity necessary to produce a cytopathic effect of 50%. The units are determined with respect to the international reference standard for Hu-IFN-beta provided by the National Institutes of Health (Pestka, S. 1986).

Every class of IFN contains several distinct types. IFN-β and IFN-γ are each the product of a single gene.

The proteins classified as IFNs-α are the most diverse group, containing about 15 types. There is a duster of IFN-α genes on chromosome 9, containing at least 23 members, of which 15 are active and transcribed. Mature IFNs-α are not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. These new types of therapeutic agents can are sometimes called biologic response modifiers (BRMs), because they have an effect on the response of the organism to the tumor, affecting recognition via immunomodulation.

Human fibroblast interferon (IFN-β) has antiviral activity and can also stimulate natural killer cells against neoplastic cells. It is a polypeptide of about 20,000 Da induced by viruses and double-stranded RNAS. From the nucleotide sequence of the gene for fibroblast interferon, cloned by recombinant DNA technology, (Derynk et al. 1980) deduced the complete amino acid sequence of the protein. It is 166 amino acid long.

Shepard et al. (1981) described a mutation at base 842 (Cys→Tyr at position 141) that abolished its anti-viral activity, and a variant clone with a deletion of nucleotides 1119-1121.

Mark et al. (1984) inserted an artificial mutation by replacing base 469 (T) with (A) causing an amino acid switch from Cys→Ser at position 17. The resulting IFN-β was reported to be as active as the "native" IFN-β and stable during long-term storage (−70° C.).

Rebif® (Serono—recombinant human interferon-β), the latest development in interferon therapy for multiple sclerosis (MS), is interferon(IFN)-beta-1a, produced from mammalian cell lines. Its recommended international Non-proprietary Name (INN) is "Interferon beta-1a".

As with all protein-based pharmaceuticals, one major obstacle that must be overcome in the use of IFN-beta as a therapeutic agent, is the loss of pharmaceutical efficacy that can result from its instability in pharmaceutical formulations.

Physical instabilities that threaten polypeptide activity and efficacy in pharmaceutical formulations include denaturation and formation of soluble and insoluble aggregates, while chemical instabilities include hydrolysis, imide formation, oxidation, racemization, and deamidation. Some of these changes are known to lead to the loss or reduction of the pharmaceutical activity of the protein of interest. In other cases, the precise effects of these changes are unknown, but the resulting degradative products are still considered to be pharmaceutically unacceptable due to the potential for undesirable side effects.

The stabilization of polypeptides in pharmaceutical compositions remains an area in which trial and error plays a major role (reviewed by Wang (1999) *Int. J. Pharm.* 185:129-188; Wang and Hanson (1988) *J. Parenteral Sci. Tech.* 42:S3-S26). Excipients that are added to polypeptide pharmaceutical formulations to increase their stability include buffers, sugars, surfactants, amino acids, polyethylene glycols, and polymers, but the stabilizing effects of these chemical additives vary depending on the protein.

Cyclodextrins are cyclic oligosaccharides. The most common cydodextrins are alpha-cyclodextrin, which is composed of a ring of six glucose residues; beta-cyclodextrin, which is composed of a ring of seven glucose residues; and gamma-cyclodextrin, which is composed of a ring of eight glucose units. The inside cavity of a cyclodextrin is lipophilic, while the outside of the cyclodextrin is hydrophilic; this combination of properties has led to widespread study of the cyclodextrins, particularly in connection with pharmaceuticals, and many inclusion complexes have been reported. Beta-cyclodextrin has been of special interest because of its cavity size, but its relatively low aqueous solubility (about 1.8% w/v at 25° C.) and attendant nephrotoxicity have limited its use in the pharmaceutical field. Attempts to modify the properties of the natural cyclodextrins have resulted in the development of heptakis (2,6-dimethyl)-beta-cyclodextrin, heptakis (2,3,6-tri-O-methyl)-beta-cyclodextrin, hydroxypropyl-beta-cyclodextrin, beta-cyclodextrin-epichlorohydrin polymer and others. For a comprehensive review of cyclodextrins and their use in pharmaceutical research, see Pitha et at, in *Controlled Drug Deliver*, ed. S. D. Bruck, Vol. I, CRC Press, Boca Raton, Fla., pp. 125-148 (1983). For an even more recent overview, see Uekama et at, in *CRC Critical Reviews in Therapeutic Drug Carrier Systems*, Vol. 3 (1), 1-40 (1987); Uekama, in *Topics in Pharmaceutical Sciences* 1987, eds. D. D. Breimer and P. Speiser, Elsevier Science Publishers B. V. (Biomedical Division), 181-194 (1987); and Pagington, *Chemistry in Britain*, pp. 455-458 (May 1987). The use of cyclodextrins specifically in the field of peptide and protein delivery has bee reviewed by T. Ide et al in *Adv. Drug Deliv. Rev*, Vol 36, 101-123 (1999) and examples in the case of ovine growth hormone, interleukin 2 and bovine Insulin are described in Brewster et al., 1991, *Phamaceutical Research*, 8(6), 792-795.

WO 90/03784 and U.S. Pat. No. 5,997,856 describe a method for the solubilization and/or stabilization of polypeptides, especially proteins, by means of cyclodextrins. However no data on the stabilization if interferons are reported in this document.

U.S. Pat. No. 6,582,728 describes dry powder compositions for pulmonary administration containing interferon-beta also containing human serum albumin, which can further contain cyclodextrins. However, even in this case no data on the stabilization of interferon composition containing also cyclodextrins are reported in this document.

WO 2003/002152 described stabilized compositions comprising an interferon molecule and a specific derivative of cyclodextrin, i.e. sulfoalkyl ether cyclodextrin.

Consequently, there is a need for additional IFN-beta pharmaceutical compositions comprising physiologically compatible stabilizers that improve the solubility of this protein and stabilize the protein against aggregate formation, thereby enhancing their pharmaceutical utility.

DESCRIPTION OF THE INVENTION

The present invention is directed to stabilized pharmaceutical compositions that comprise an Interferon (IFN), methods for their preparation and use thereof. In particular the main object of the invention is to provide a stabilized liquid pharmaceutical composition comprising an interferon (IFN) or an isoform, mutein, fused protein, functional derivative, active fraction or salt thereof, wherein said formulation is a solution that comprises a buffer, a cyclodextrin, preferably an isotonicity agent and an anti-oxidant.

The compositions are preferably prepared in the absence of hum an serum albumin (HSA), and are thus free of this pharmaceutical excipient. Such compositions are referred to herein as "HSA-free" IFN pharmaceutical compositions and they comprise an interferon (IFN) or an isoform, mutein, fused protein, functional derivative, active fraction or salt thereof.

According to an embodiment of the present invention the compositions also comprise a bacteriostatic agent.

An "interferon" or "IFN", as used herein, is intended to include any molecule defined as such in the literature, comprising for example any types of IFNs mentioned in the above section "Background of the invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex®) (Biogen) or Betaferon® (Schering). The use of interferons of human origin is also preferred in accordance with the present invention. The term interferon, as used herein, is intended to encompass salts, functional derivatives, variants, analogs and active fragments thereof.

The term "Interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably IFN-beta is intended to mean Interferon beta-1a.

As used herein the term "muteins" refers to analogs of IFN in which one or more of the amino acid residues of a natural IFN are replaced by different amino acid residues, or are deleted, or one or more amino acid residues are added to the natural sequence of IFN, without changing considerably the activity of the resulting products as compared to the wild type IFN. These muteins are prepared by known synthesis and/or by site-directed mutagenesis techniques, or any other known technique suitable therefore. Preferred muteins include e.g. the ones described by Shepard et al. (1981) or Mark et al. (1984).

Any such mutein preferably has a sequence of amino acids sufficiently duplicative of that of IFN, such as to have substantially similar or even better activity to an IFN. The biological function of interferon is well known to the person skilled in the art, and biological standards are established and available e.g. from the National Institute for Biological Standards and Control (See Worldwide Website: immunology.org/links/NIBSC).

Bioassays for the determination of IFN activity have been described. An IFN assay may for example be carried out as described by Rubinstein et al., 1981. Thus, it can be determined whether any given mutein has substantially a similar, or even a better, activity than IFN by means of routine experimentation.

Muteins of IFN, which can be used in accordance with the present invention, or nucleic acid coding therefore, include a finite set of substantially corresponding sequences as substitution peptides or polynucleotide's which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of polypeptides or proteins of the invention, may include synonymous amino acids within a group, which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino adds which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino add groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |

TABLE III-continued

Most Preferred Groups of Synonymous Amino Acids

| Amino Acid | Synonymous Group |
|---|---|
| Glu | Glu |
| Met | Met, Ile, Leu |
| Trp | Met |

Examples of production of amino acid substitutions in proteins which can be used for obtaining muteins of IFN, for use in the present invention include any known method steps, such as presented in U.S. Pat. Nos. 4,959,314, 4,588,585 and 4,737,462, to Mark et al. U.S. Pat. No. 5,116,943 to Koths et al., U.S. Pat. No. 4,965,195 to Namen et al. U.S. Pat. No. 4,879,111 to Chong et al; and U.S. Pat. No. 5,017,691 to Lee et al. and lysine substituted proteins presented in U.S. Pat. No. 4,904,584 (Shaw et al). Specific muteins of IFN-beta have been described, for example by Mark et al., 1984.

The term "fused protein" refers to a polypeptide comprising an IFN, or a mutein thereof, fused to another protein, which e.g., has an extended residence time in body fluids. An IFN may thus be fused to another protein, polypeptide or the like, e.g., an immunoglobulin or a fragment thereof.

"Functional derivatives" as used herein cover derivatives of IFN, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity IFN, and do not confer toxic properties on compositions containing it. These derivatives may, for example, include polyethylene glycol side-chains, which may mask antigenic sites and extend the residence of IFN in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of IFN, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding IFN.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric add, and salts with organic adds, such as, for example, acetic acid or oxalic add. Of course, any such salts must retain the biological activity of the proteins (IFN) relevant to the present invention, i.e., the ability to bind to the corresponding receptor and initiate receptor signaling.

In accordance with the present invention, the use of recombinant human IFN-beta and the compounds of the invention is further particularly preferred.

A special kind of interferon variant has been described recently. The so called "consensus interferons" are non-naturally occurring variants of IFN (U.S. Pat. No. 6,013,253). According to a preferred embodiment of the invention, the compounds of the invention are used in combination with a consensus interferon.

As used herein, human interferon consensus (IFN-con) shall mean a non-naturally-occurring polypeptide, which predominantly includes those amino acid residues that are common to a subset of IFN-alpha's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not existent in that position in at least one naturally-occurring subtype. IFN-con encompasses but is not limited to the amino add sequences designated IFN-con1, IFN-con2 and IFN-con3 which are disclosed in U.S. Pat. Nos. 4,695,623, 4,897,471 and 5,541,293. DNA sequences encoding IFN-con may be produced as described in the above-mentioned patents, or by other standard methods.

In a further preferred embodiment, the fused protein comprises an Ig fusion. The fusion may be direct, or via a short linker peptide which can be as short as 1 to 3 amino acid residues in length or longer, for example, 13 amino acid residues in length. Said linker may be a tripe tide of the sequence E-F-M (Glu-Phe-Met) (SEQ ID:1), for example, or a 13-amino acid linker sequence comprising Glu-Phe-Gly-Ala-Gly-Leu-Val-Leu-Gly-Gly-Gln-Phe-Met (SEQ ID:2) introduced between the sequence of IFN and the Immunoglobulin sequence. The resulting fusion protein may have improved properties, such as an extended residence time in body fluids (half life), increased specific activity, increased expression level, or the purification of the fusion protein is facilitated.

In a further preferred embodiment, IFN is fused to the constant region of an $IgG_2$ molecule. Preferably, it is fused to heavy chain regions, like the $CH_2$ and $CH_3$ domains of human $IgG_1$, for example. Other isoforms of Ig molecules are also suitable for the generation of fusion proteins according to the present invention, such as isoforms $IgG_2$, $IgG_3$ or $IgG_4$, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO 99/55377, for example.

The dosage administered, as single or multiple doses, to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

Standard dosages of human IFN-beta range from 80 000 IU/kg and 200 000 IU/kg per day or 6 MIU (million international units) and 12 MIU per person per day or 22 to 44 µg (microgram) per person. In accordance with the present invention, IFN may preferably be administered at a dosage of about 1 to 50 μg, more preferably of about 10 to 30 μg or about 10 to 20 μg per person per day.

The administration of active ingredients in accordance with the present invention may be by intravenous, intramuscular or subcutaneous route. The preferred route of administration for IFN is the subcutaneous route.

IFN may also be administered daily or every other day, or less frequently. Preferably, IFN is administered one, twice or three times per week.

The preferred route of administration is subcutaneous administration, administered e.g. three times a week. A further preferred route of administration is the intramuscular administration, which may e.g. be applied once a week.

The dosing of IFN-β In the treatment of relapsing-remitting MS according to the invention depends on the type of IFN-β used.

In accordance with the present invention, where IFN is recombinant IFN-β1b produced in E. Coli, commercially available under the trademark Betaseron®, it may preferably be administered sub-cutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intra-muscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 μg or 6 MIU to 12 MIU per person.

The term "stability" refers to the physical, chemical, and conformational stability of formulations of interferon of the present invention (including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of an interferon polypeptide included in the present invention.

A "stable" or "stabilized" solution or formulation, is one wherein the degree of degradation, modification, aggregation, loss of biological activity and the like, of proteins therein is acceptably controlled, and does not increase unacceptably with time. Preferably the formulation retains at least at or about 60%, more preferably at least at or about 70%, most preferably at least at or about 80% of the labelled interferon activity over a period of 24 months. The stabilized IFN compositions of the invention preferably have a shelf-life of at least about 6 months, 12 months, 18 months, more preferably at least 20 months, still more preferably at least about 22 months, most preferably at least about 24 months when stored at 2-8° C.

Methods for monitoring stability of the IFN pharmaceutical compositions of the invention are available in the art, including those methods described in the examples disclosed herein. Thus, IFN aggregate formation during storage of a liquid pharmaceutical composition of the invention can be readily determined by measuring the change in soluble IFN in solution over time. Amount of soluble polypeptide in solution can be quantified by a number of analytical assays adapted to detection of IFN. Such assays include, for example, size exclusion chromatography (SEC)-HPLC and UV absorption spectroscopy, as described in the Examples below.

Determination of both soluble and insoluble aggregates during storage in liquid formulations can be achieved, for example, using analytical ultracentrifugation as noted in the Examples below to distinguish between that portion of the soluble polypeptide that is present as soluble aggregates and that portion that is present in the nonaggregate, biologically active molecular form.

The expression "multi-dose use" is intended to include the use of a single vial, ampoule or cartridge of an interferon formulation for more than one injection, for example 2, 3, 4, 5, 6 or more injections. The injections are preferably made over a period of at least at or about 12 hours, 24 hours, 48 hours, etc., preferably up to a period of at or about 12 days. The injections may be spaced in time, for example, by a period of 6, 12, 24, 48 or 72 hours.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino 2-hydroxymethyl 1,3,-propanediol, and to any pharmacologically acceptable salt thereof. Preferable buffers are acetate buffers with saline or an acceptable salt.

The "cyclodextrins" contemplated for use herein are hydroxypropyl, hydroxyethyl, glucosyl, maltosyl and maltotriosyl derivatives of beta-cyclodextrin and the corresponding derivatives of gamma-cyclodextrin. The hydroxyalkyl groupings may contain one or more hydroxyl groups, e.g. hydroxypropyl (2-hydroxypropyl, 3-hydroxypropyl), dihydroxypropyl and the like. The glucosyl, maltosyl and maltotriosyl derivatives may contain one or more sugar residues, e.g. glucosyl or diglucosyl, maltosyl or dimaltosyl. Various mixtures of the cyclodextrin derivatives may be used as well, e.g. a mixture of maltosyl and dimaltosyl derivatives. Specific cyclodextrin derivatives for use herein include hydroxypropyl-beta-cyclodextrin (HPCD or HPBCD), hydroxyethyl-beta-cyclodextrin (HEBCD), hydroxypropyl-gaamma-cyclodextrin (HPGCD), hydroxyethyl-gamma-cyclodextrin (HEGCD), dihydroxypropyl-beta-cyclodextrin (2HPBCD), glucosyl-beta-cyclodextrin ($G_1$-beta-CD or GlBCD), diglucosyl-beta-cyclodextrin (2G $G_1$-beta-CD or 2 $G_1$BCD), maltosyl-beta-cyclodextrin ($G_2$-beta-CD or $G_2$BCD), maltosyl-gamma-cyclodextrin ($G_2$-gamma-CD or $G_2$GCD), maltotriosyl-beta-cyclodextrin ($G_3$-beta-CD or $G_3$BCD), maltotriosylgamma-cyclodextrin ($G_3$-gamma-CD or $G_3$GCD) and dimaltosyl-beta-cyclodextrin (2 $G_2$-beta-CD or 2 $G_2$BCD), and mixtures thereof such as maltosyl-beta-cydodextrin/dimaltosyl-beta-dodextrin.

Hydroxypropyl-beta-cyclodextrin for use in the compositions of the present invention is commercially available and is the preferred cyclodextrin according to the invention.

Alternatively, it may be prepared by known methods, especially by use of the optimized procedure of Pitha et al, *International Journal of Pharmaceutics*, 29, 73-82 (1986).

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable isotonicity agents include, but are not limited to, amino acids or proteins (e.g., glycine or albumin), salts (e.g., sodium chloride), and sugars (e.g., dextrose, mannitol, sucrose and lactose). Preferably the isotonicity agent is mannitol.

The term "antioxidant" refers to a compound that prevents oxygen or oxygen-derived free radicals from interacting with other substances. Antioxidants are among a number of excipients commonly added to pharmaceutical systems to enhance physical and chemical stability. Antioxidants are added to minimize or retard oxidative processes that occur with some drugs or excipients upon exposure to oxygen or in the presence of free radicals. These processes can often be catalyzed by light, temperature, hydrogen on concentration, presence of trace metals or peroxides. Sulfites, bisufrites, thiourea, methionine, salts of ethylenediaminetetraacetic acid (EDTA), butylated hydroxytoluene (BHT), and butylated hydroxy anisole (BHA) are frequently used as antioxidants in drugs. Sodium EDTA has been found to enhance the activity of antioxidants by chelating metallic ions that would otherwise catalyze the oxidation reaction. Most preferred antioxidant is methionine.

The term "bacterostatic" refers to a compound or compositions added to a formulation to act as an anti-bacterial agent. A preserved interferon-containing formulation of the present invention preferably meets statutory or regulatory guidelines for preservative effectiveness to be a commercially viable multi-use product Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Preferably the bacteriostatic agent is benzyl alcohol.

In a preferred embodiment, the invention provides a stabilized liquid pharmaceutical composition comprising an interferon (IFN) or an isoform, mutein, fused protein, functional derivative, active fraction or salt thereof, wherein said formulation is a solution that comprises a buffer, 2-hydroxypropyl-beta-cyclodextrin, an isotonicity agent and an anti-oxidant.

In a further preferred embodiment, the invention provides a stabilized liquid pharmaceutical composition wherein said interferon is IFN-beta such as recombinant human IFN-beta.

In another preferred embodiment, the invention provides a stabilized liquid pharmaceutical composition wherein said buffer is present in an amount sufficient to maintain the pH of said composition within plus or minus 0.5 units of a specified pH, where the specified pH is about 3 to about 6, such as a pH value at or about 3.0 to about 6.0, including a pH value at or about 3.8.

In another preferred embodiment, the invention provides a stabilized liquid pharmaceutical composition wherein said buffer is present at a concentration of about 5 mM to 500 mM such as a concentration at or about 50 mM.

In another preferred embodiment, the invention provides a stabilized liquid pharmaceutical composition wherein the buffer is an acetate buffer.

In another preferred embodiment, the invention provides a stabilized liquid pharmaceutical composition wherein said isotonicity agent is mannitol.

In another preferred embodiment, the invention provides a stabilized liquid pharmaceutical composition wherein said isotonicity agent is present at a concentration of about 0.5 mg/ml to about 500 mg/ml, such as a concentration of or about 50 mg/ml.

In another preferred embodiment, the invention provides a stabilized liquid pharmaceutical composition wherein the antioxidant is methionine.

In another preferred embodiment, the invention provides a stabilized liquid pharmaceutical composition wherein said the antioxidant is present at a concentration of about 0.01 to about 5 mg/ml, including concentrations of about 0.01 to about 5.0 mg/ml, such as of a concentration of or about 0.1 mg/ml.

In another preferred embodiment, the invention provides a stabilized liquid pharmaceutical composition wherein said interferon is present at a concentration of about 10 µg/ml to about 800 µg/ml, such as a concentration of or about 44, 88 or 276 µg/ml.

In another preferred embodiment, the invention provides a stabilized liquid pharmaceutical composition wherein said cyclodextrin is present at a molar ratio vs. interferon of from about 500-fold molar excess up to about 700-fold molar excess.

In another preferred embodiment, the invention provides a stabilized liquid pharmaceutical composition wherein said composition is an aqueous solution.

In another preferred embodiment, the invention provides a stabilized liquid pharmaceutical composition wherein the composition of any preceding claims, further comprising a bacteriostatic agent such as benzyl alcohol.

In another preferred embodiment, the invention provides a stabilized liquid pharmaceutical composition wherein the composition of any preceding claims, further comprising a bacteriostatic agent and wherein said bacteriostatic agent is present at a concentration of about 0.1% to about 2%, including concentrations at or about 0.1% to about 2.0%, such as concentrations at or about 0.2 or about 0.3%.

In a further preferred embodiment, the invention provides a stabilized liquid pharmaceutical composition wherein the isotonicity agent is mannitol, the anti-oxidant is methionine and the interferon is interferon beta.

In another further preferred embodiment, the invention provides a stabilized liquid pharmaceutical composition wherein the composition is the following liquid formulation:

| | |
|---|---|
| Interferon beta-1a | 44 µg/mL |
| HPBCD | 1.9 mg/mL |
| Methionine | 0.1 mg/mL |
| Mannitol | 50 mg/mL |
| acetate buffer up to | 1 mL |

In another embodiment, the invention provides a method for preparing a stabilized liquid pharmaceutical composition according to the invention, wherein said method comprises adding calculated amounts of 2-hydroxypropyl-beta-cyclodextrin, antioxidant and isotonicity agent to the buffered solution and then adding the interferon (IFN) or an isoform, mutein, fused protein, functional derivative, active fraction or salt thereof.

In another embodiment, the invention provides a container hermetically sealed in conditions sterile and appropriate for storage prior to use, comprising the liquid pharmaceutical formulation according to the invention. Example of such a container are a vial or a cartridge for an auto-injector. Containers according to the invention are for mono-dose or multi-dose administration.

In a preferred embodiment, the invention provides a container according to the invention wherein said container is a pre-filled syringe for mono-dose administration.

In another embodiment, the invention provides a kit for multi-dose administration of a pharmaceutical composition according to the invention, wherein the kit comprises a first container filled with a pharmaceutical composition according to the invention and a second cartridge filled of a solution of the bacteriostatic agent.

Preferably the concentration of IFN beta in the formulation is at or about 10 μg/ml to at or about 800 μg/ml, more preferably at or about 20 μg/ml to at or about 500 μg/ml, more particularly preferably at or about 30 to at or about 300, most preferably at or about 44, 88 or 264 μg/ml.

Preferably the formulations of the present invention have pH between about 3.0 and at or about 4.5, more preferably at or about 3.8. A preferred buffer is acetate, with preferred counterions being sodium or potassium ions. Acetate saline buffers are well known in the are buffer concentrations in total solution can vary between at or about 5 mM, 9.5 mM, 10 mM, 50 mM, 100 mM, 150 mM, 200 mM, 250 mM, and 500 mM. Preferably the buffer concentration is at or about 10 mM. Particularly preferred is a buffer 50 mM in acetate ions with a pH of 3.8.

Preferably in the composition of the invention the antioxidant, for example methionine, is present at a concentration of at or about 0.01 to at or about 5 mg/ml, more preferably at or about 0.05 to at or about 0.3 mg/ml, most preferably at or about 0.1 mg/ml.

Preferably the concentration of the isotonicity agent (for example mannitol) in liquid formulations is at or about 0.5 mg/ml to at or about 500 mg/ml, more preferably at or about 1 mg/ml to at or about 250 mg/ml, more particularly preferably at or about 10 mg/ml to at or about 100 mg/ml, most preferably at or about 50 mg/ml.

In a further preferred embodiment, the invention provides a composition according to the invention wherein the isotonicity agent is mannitol, the antioxidant is methionine and the interferon is interferon beta.

In another preferred embodiment, the invention provides a composition according to the invention wherein the liquid composition is the following:

| | |
|---|---|
| Interferon beta-1a | 44 μg/mL |
| HPBCD | 1.9 mg/mL |
| Methionine | 0.1 mg/mL |
| Mannitol | 50 mg/mL |
| acetate buffer up to | 1 mL |

The invention includes liquid formulations. The preferred solvent is water for injection.

Liquid formulations may be mono-dose or multi-dose. Those liquid interferon formulations of the invention that are intended for multi-dose use preferably comprise a bacteriostatic, such as phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Particularly preferred are phenol, benzyl alcohol and m-cresol, more preferred is benzyl alcohol. The bacteriostatic agent is used in an amount that will yield a concentration that is effective to maintain the formulation essentially bacteria free (suitable for injection) over the multi-dose injection period, which may be at or about 12 or 24 hours to at or about 12 days, preferably at or about 6 to at or about 12 days. The bacteriostatic is preferably present in a concentration of at or about 0.1% (mass bacteriostatic/mass of solvent) to at or about 2.0%, more preferably at or about 0.2% to at or about 1.0%. In the case of benzyl alcohol, particularly preferred are concentrations of 0.2 or 0.3%).

The bacteriostatic may also be present in mono-dose formulations.

The range of interferon in the formulations of the invention includes amounts yielding upon reconstitution, concentrations from about 1.0 μg/ml to about 50 mg/ml, although lower and higher concentrations are operable and are dependent on the intended delivery vehicle, e.g., solution formulations will differ from transdermal patch, pulmonary, transmucosal, or osmotic or micro pump methods. The interferon concentration is preferably at or about 5 μg/ml to at or about 2 mg/ml, more preferably at or about 10 μg/ml to at or about 1 mg/ml, most preferably at or about 30 μg/ml to at or about 100 μg/ml.

Preferably the formulations of the invention retain at least at or about 60%, more preferably at least at or about 70%, most preferably at least at or about 80% of the interferon activity at the time of packaging over a period of 24 months.

In a further preferred embodiment, the invention provides a method for manufacturing a liquid pharmaceutical composition as described before.

In yet another preferred embodiment, the invention provides a method for manufacturing a packaged pharmaceutical composition comprising placing a solution comprising the active ingredient and the excipients as described before.

In yet another preferred embodiment, the invention provides an article of manufacture for human pharmaceutical use, comprising a vial comprising the pharmaceutical compositions as described before, and written material stating that such solution may be held over a period of at or about twenty-four hours or greater after the first use. Preferably the written material states that the solution may be held up to at or about 12 days.

After the first use of a multi-dose formulation it may be kept and used for at least at or about 24 hours, preferably at least at or about 4, 5 or 6 days, more preferably for up to 12 days. After the first use the formulation it is preferably stored at below room temperature (i.e. below at or about 25° C.), more preferably below at or about 10° C., more preferably at or about 2-8° C., most preferably at or about 5° C.

The formulations of the present invention can be prepared by a process which comprises adding the calculated amounts of the excipients to the buffered solution and then adding the interferon.

The resulting solution is then placed in vials, ampoules or cartridges. Variations of this process would be recognized by one of ordinary skill in the art. For example, the order the components are added, whether additional additives are used, the temperature and pH at which the formulation is prepared, are all factors that may be optimised for the concentration and means of administration used.

In case of a multi-dose use formulation, the bacteriostatic agent may be added to the solution containing the active ingredient (interferon) or alternatively may be kept in a separate vial or cartridge and subsequently mixed to the solution containing the active ingredient at the moment of use.

The formulations of the invention can be administered using recognized devices. Examples comprising these single vial systems include auto-injector or pen-injector devices for delivery of a solution such as Rebiject®.

The products presently claimed include packaging material. The packaging material provides, in addition to the information required by the regulatory agencies, the conditions under which the product may be used. The packaging material of the present invention provides instructions to the patient, if needed, to prepare the final solution and to use such final solution over a period of twenty-four hours or greater for the two vial, wet/dry, product. For the single vial, solution product, the label indicates that such solution may be used over a period of twenty-four hours or greater. The presently claimed products are useful for human pharmaceutical product use.

The stable preserved formulations may be provided to patients as clear solutions. The solution may be for single use or it may be reused multiple times and may suffice for a single or multiple cycles of patient treatment and thus provides a more convenient treatment regimen than currently available.

The interferon in either the stable or preserved formulations or solutions described herein, may be administered to a patient in accordance with the present invention via a variety of delivery methods including SC or IM injection; transdermal, pulmonary, transmucosal, implant, osmotic pump, cartridge, micro pump, oral, or other means appreciated by the skilled artisan, as well-known in the art.

The term "vial" refers broadly to a reservoir suitable for retaining interferon in solid or liquid form in a contained sterile state. Examples of a vial as used herein include ampoules, cartridges, blister packages, or other such reservoir suitable for delivery of the interferon to the patient via syringe, pump (including osmotic), catheter, transdermal patch, pulmonary or transmucosal spray. Vials suitable for packaging products for parenteral, pulmonary, transmucosal, or transdermal administration are well known and recognized in the art.

The term "treatment" within the context of this invention refers to any beneficial effect on progression of disease, including attenuation, reduction, decrease or diminishing of the pathological development after onset of disease.

Pharmaceutical compositions of the invention comprising IFN or an isoform, mutein, fused protein, functional derivative, active fraction or salt are useful in the diagnosis, prevention, and treatment (local or systemic) of clinical indications responsive to therapy with this polypeptide. Such clinical indications include, for example, disorders or diseases of the central nervous system (CNS), brain, and/or spinal cord, including multiple sclerosis; autoimmune diseases, including rheumatoid arthritis, psoriasis, Crohn's disease; and cancers, including breast, prostate, bladder, kidney and colon cancers.

In one embodiment, the invention include the use of compositions of the invention for the preparation of a pharmaceutical formulation for the treatment of disorders or diseases affecting the central nervous system (CNS) disorders, brain, and/or spinal cord, including multiple sclerosis; autoimmune diseases, including rheumatoid arthritis, psoriasis, Crohn's disease; and cancers, including breast, prostate, bladder, kidney and colon cancers.

In another embodiment, the invention provides a method of treatment of disorders or diseases affecting the central nervous system (CNS) disorders, brain, and/or spinal cord, including multiple sclerosis; autoimmune diseases, including rheumatoid arthritis, psoriasis, Crohn's disease; and cancers, including breast, prostate, bladder, kidney and colon cancers, comprising the administration of composition of the invention in a patient in need thereof.

In another embodiment of the invention, the compositions of the invention are useful for the treatment of disorders or diseases affecting the central nervous system (CNS) disorders, brain, and/or spinal cord, including multiple sclerosis; autoimmune diseases, including rheumatoid arthritis, psoriasis, Crohn's disease; and cancers, including breast, prostate, bladder, kidney and colon cancers.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

In the table the alpha helix residual in the range of 200-260 nm has been considered for the comparison of IFN conformational stability in the pre/post melting CDNN deconvolutions (average of four analyses).

Figure 7:
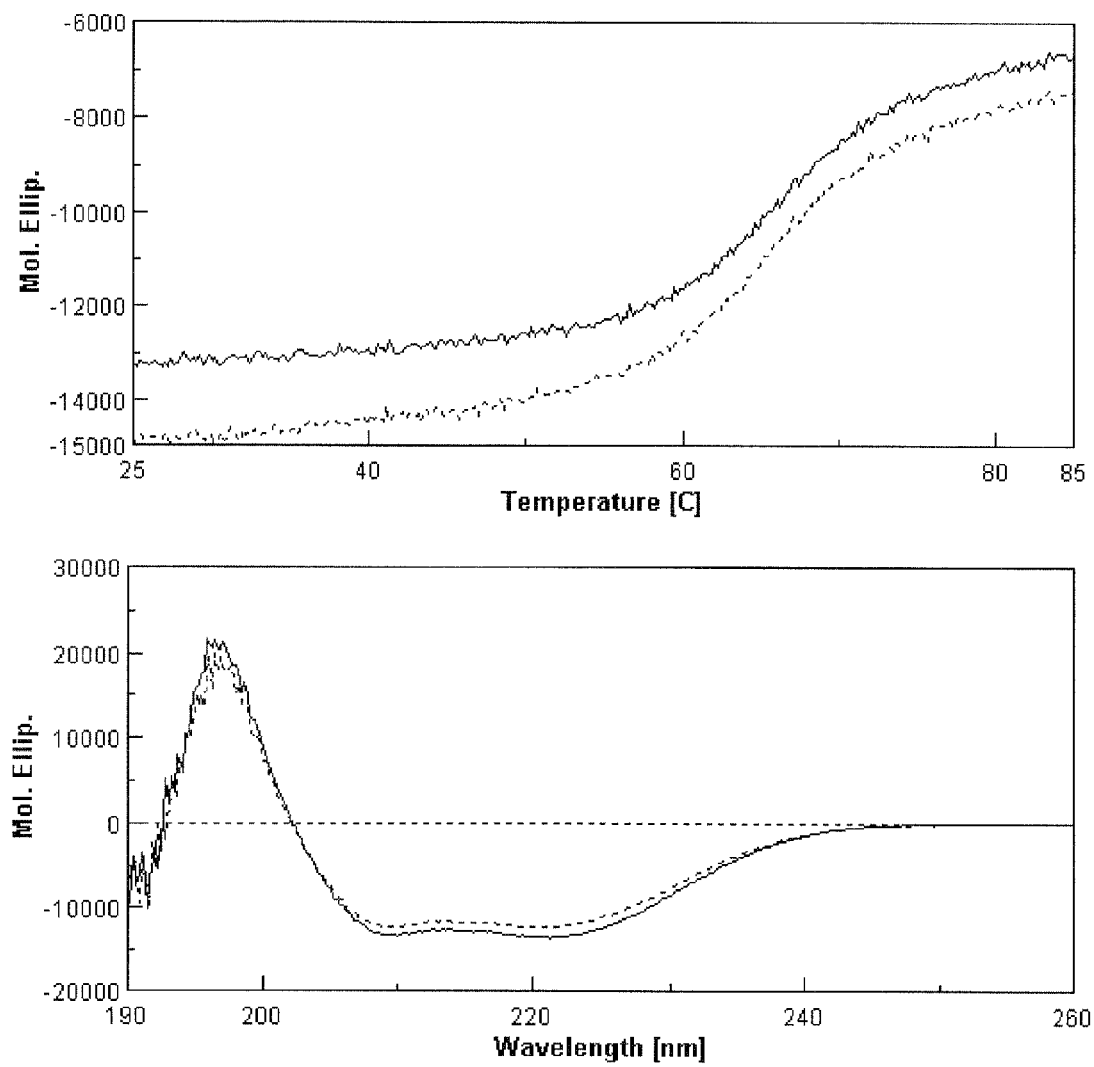

FIG. 7: the thermal denaturation curve is reported for a solution containing interferon beta-1a about 44 μg/mL and HPBCD 2.11 mg/mL (700-fold molar excess with respect to molar amount of interferon beta-1a), i.e. the effect of temperature on CD signal at 222 nm, expressed as molar ellipticity, deg $M^{-1}$ $cm^{-1}$. In the upper part of the figure (solid line), compared with the protein alone (dash line) and the relative CD spectrum before (solid line) and after (dash line) melting transition in the lower part of the figure. Hereinafter the respective CDNN (Circular Dichroism Neural Network) deconvolutions (average of three analyses) are reported.

Figure 8:
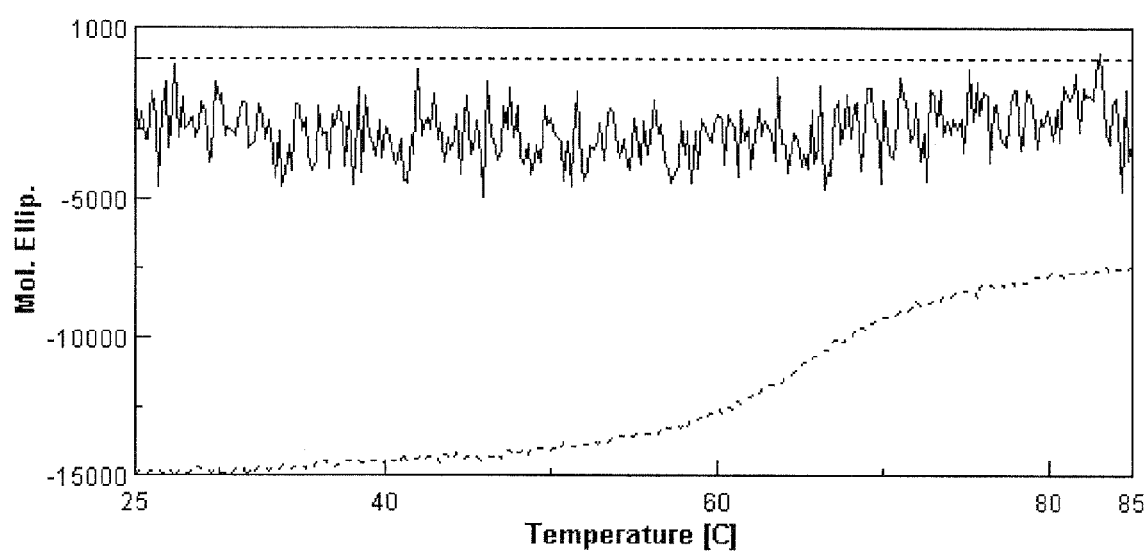

FIG. 8: it shows the thermal denaturation of interferon beta-1a alone (dash curve) and in the presence of Na L-ascorbate 500-fold molar excess with respect to molar amount of interferon beta-1a (solid curve).

Figure 9:
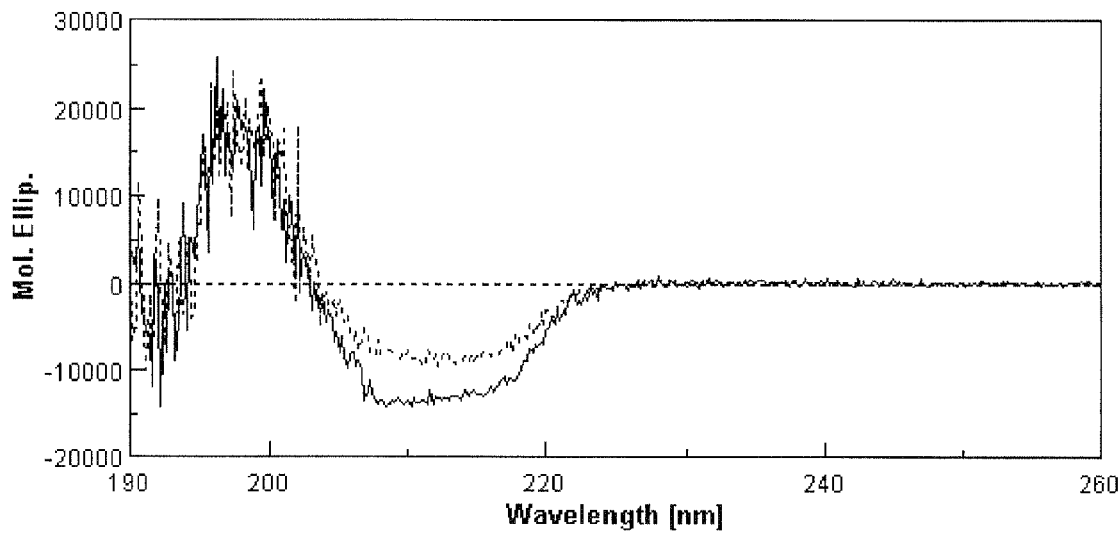

FIG. 9: it shows [interferon beta-1a/ascorbate 500×] CD spectrum before (solid curve) and after (dash curve) meting transition and respective CDNN deconvolutions (see above).

Figure 10:
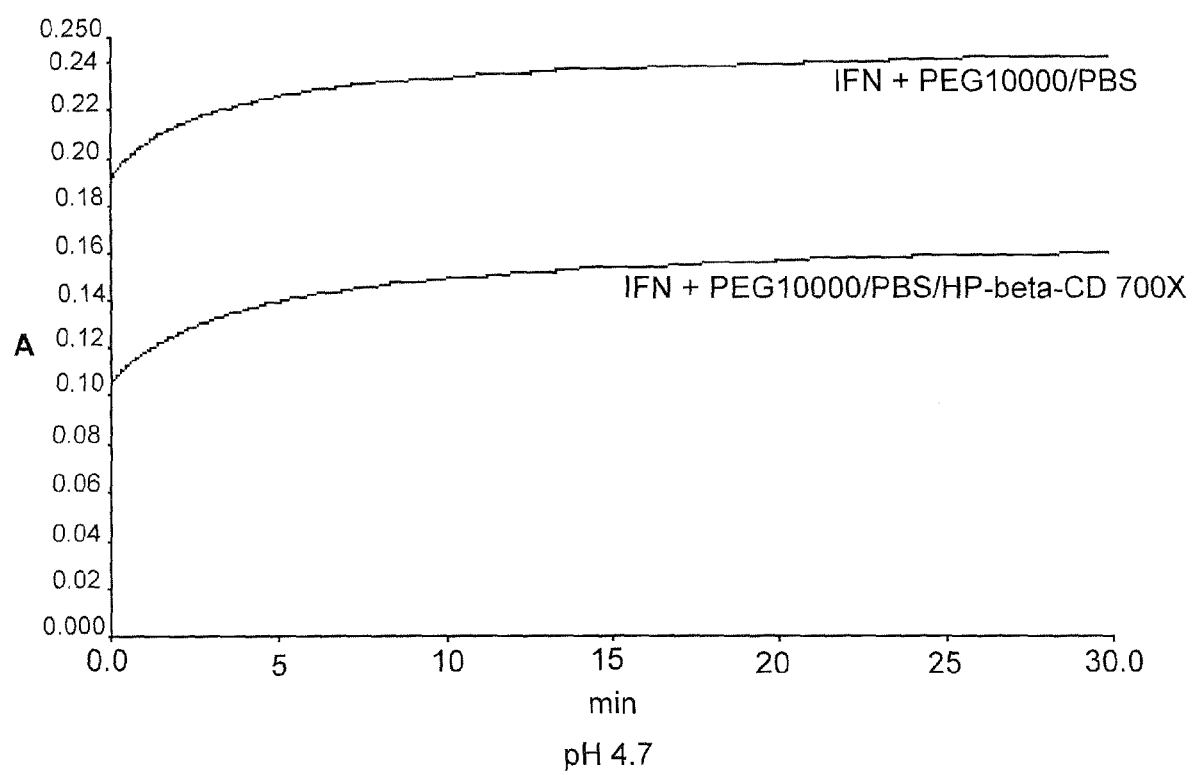

FIG. 10: it shows the aggregation kinetic of interferon beta-1a 0.116 mg/mL (5.16 μM) in PEG/PBS (final pH=4.7) after incubation at 62+/−2° C. 10 min. and the effect of a 700× M excess of HPBCD (5.56 mg/mL). In the Y axis is reported the optical density measured at 360 nm which is directly proportional to turbidimertry.

Figure 11:
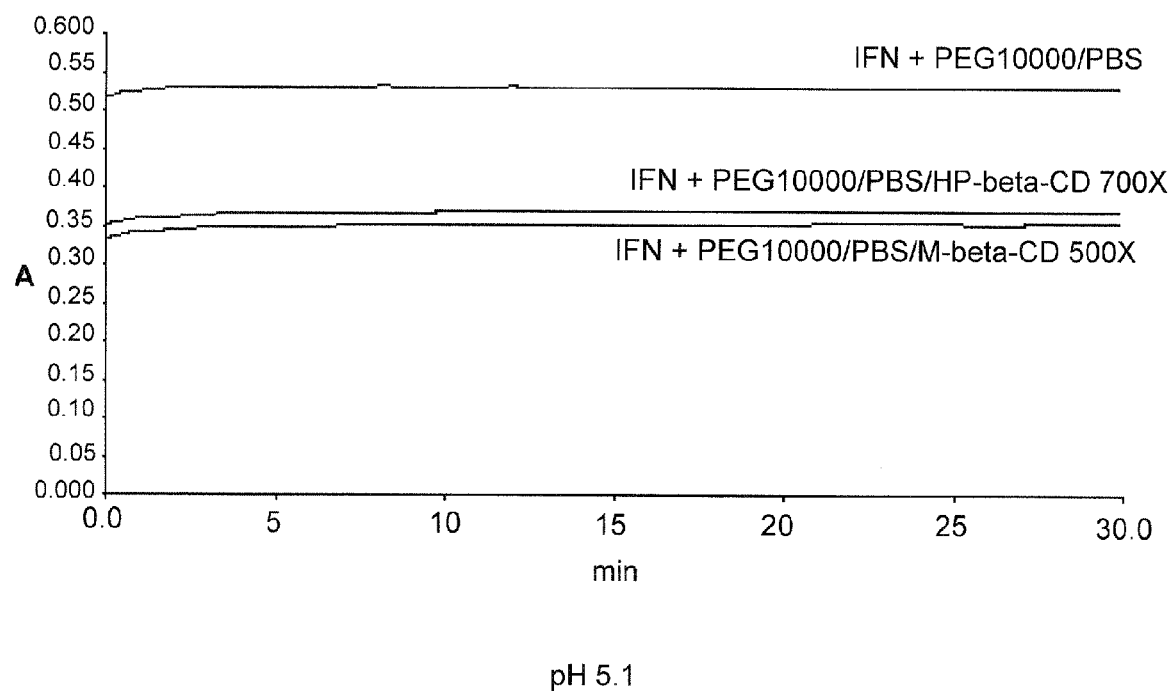

FIG. 11: it shows the aggregation kinetic of interferon beta-1a 0.116 mg/mL (5.16 μM) in PEG/PBS (final pH=5.1) after incubation at 62+/−2° C. 10 min. and the effect of a 700× M excess of HPBCD (5.56 mg/mL) and 5(0× M excess of RMBCD (3.38 mg/mL).

Figure 12:
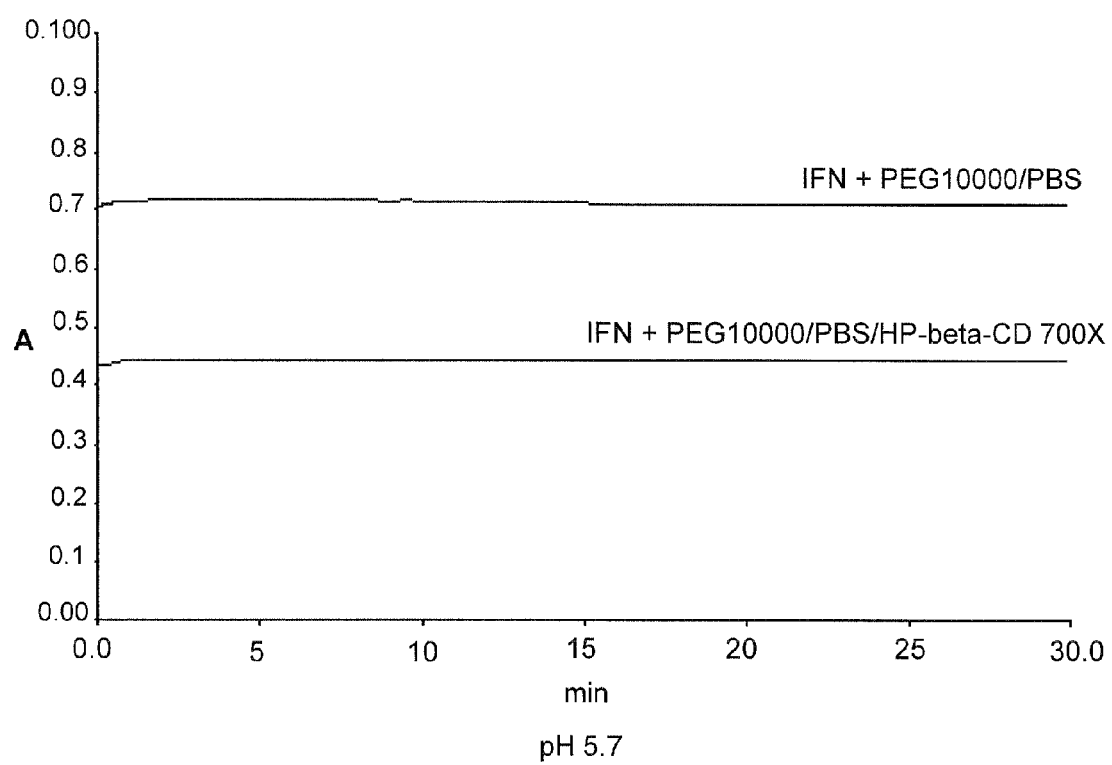

FIG. 12: it shows the aggregation kinetic of interferon beta-1a 0.116 mg/mL (5.16 μM) in PEG/PBS (final pH=5.7) after incubation at 62+/−2° C. 10 min. and the effect of a 700× M excess of HPBCD (5.56 mg/mL).

EXAMPLES

The following abbreviations refer respectively to the definitions below:

cm (centimeter), mg (milligram), μg (microgram), min (minute), mM (millimolar), mL (milliliter), nm (nanometer), BHT (butylated hydroxytoluene), CD (Circular dichroism), EDTA (ethylenediaminetetraacetic acid), HPBCD (Hydroxypropyl-beta-cyclodextrin), HPLC (High Performance Liquid Chromatography), IFN (interferon), IM (intra-muscular), OD (Optical Density), PBS (Phosphate Buffered Saline), PEG (Polyethylene glycol), RMBCD (randomly substituted methyl-beta-cyclodextrin), SC (subcutaneous), TFA (trifluoro-acetic acid), TRIS (2-amino 2-hydroxymethyl-1,3 propanediol), UV (Ultraviolet), WFI (Water For Injection).

Methods

Turbidimetry Measurements

Protein aggregation was monitored for 30 min at 360 nm using an UV-visible spectrophotometer system (Perkin Elmer Lambda 40).

Preliminary studies established operative conditions under which the protein displays appropriate aggregation behaviour, that is dilution of interferon beta-1a bulk 1:2 with a solution of PEG 10,000 30 mg/mL in PBS (0.2 μm Ø filtered), in a polypropylene vial, followed by incubation in a thermostatic water bath at T=62±2° C. for 10 min.

Heating and PEG were used in order to enhance the protein association process through thermal denaturation and exclusion volume effect, respectively. The UV-visible analysis was performed in a cell containing a sample volume of 3 mL (final interferon beta-1a concentration=0.116 mg/mL).

Each turbidity analysis was repeated at least in triplicate and the optical density $(OD)_{360\ nm}$ versus time average curve is reported. Aggregation of the protein alone was compared to interferon beta-1a in the presence of excipients at different concentrations.

Circular Dichroism Measurements

CD measurements were performed with a Jasco J810 spectropolarimeter equipped with a Peltier temperature controller. Samples were contained in a stoppered 1 cm quartz cell and, for thermal scans, magnetic stirring rate was of about 150 rpm.

For the far-UV spectrum (260-185 nm), a protein concentration of about 44 μg/mL, a resolution of 0.2 nm and a scanning speed of 2 nm/min with a 2 seconds response time and 3 accumulations were employed.

In order to monitor the thermal perturbation of secondary structure of interferon beta-1a, CD signal at 222 nm as a function of temperature was followed between 25° C. and 85° C. at 0.2° C. intervals, using a 1° C./min temperature ramp rate and a delay time of 60 seconds.

Each measurement was performed at least in triplicate on interferon beta-1a bulk, as a control, and on interferon beta-1a solutions containing different concentrations of excipients.

Size Exclusion Cromatography (Sec) Analysis

Liquid interferon beta-1a formulations at pre-fixed time-points of the stability studies, were analysed by SE-HPLC in order to determine interferon beta-1a purity and assay (expressed as recovery %).

Figure 1:
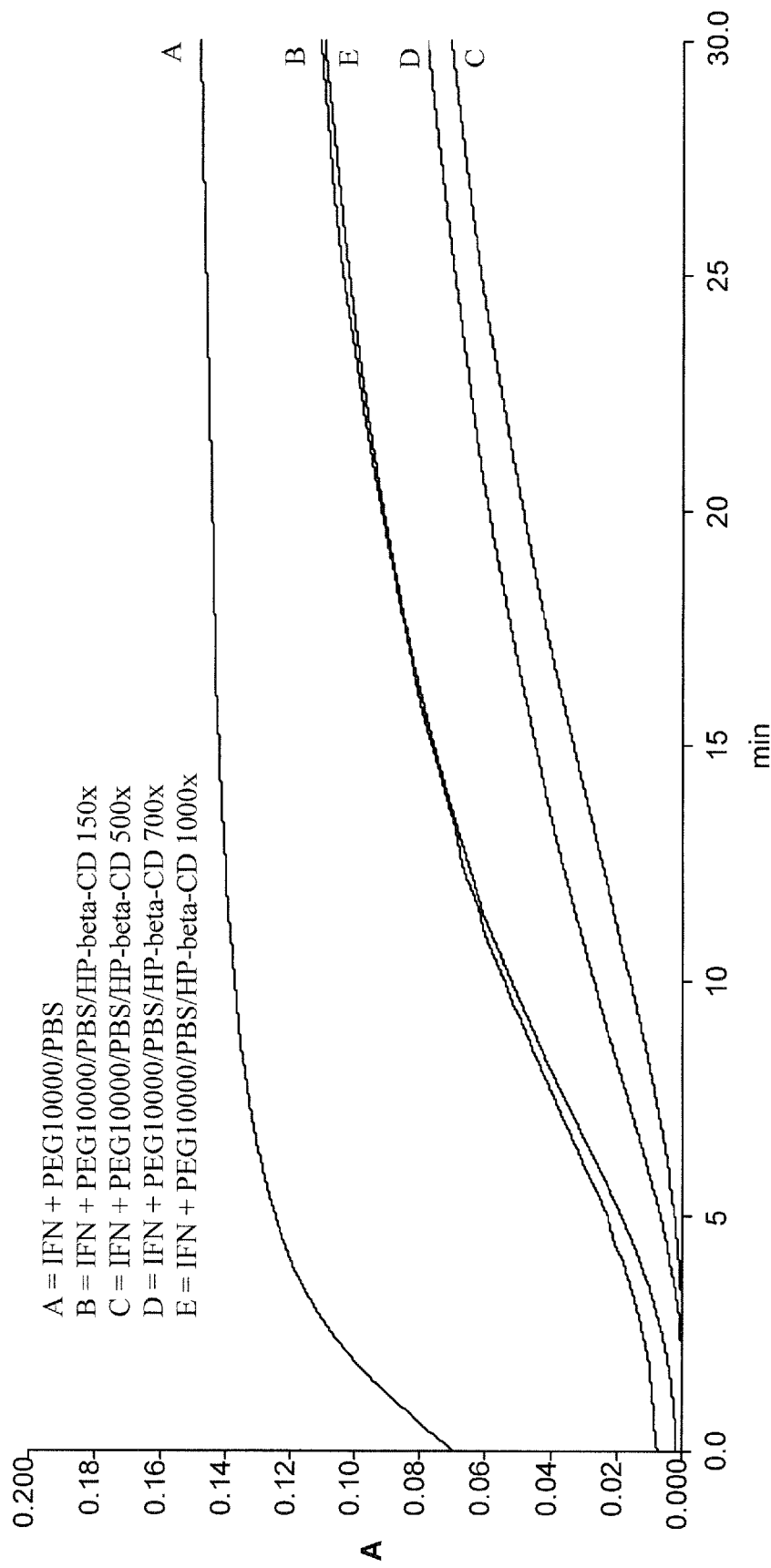
FIG. 1: it shows the aggregation kinetic of interferon beta-1 a 0.116 mg/mL (5.16 µM) in PEG/PBS, after incubation at 62+/−2° C. 10 min., in the presence of different concentrations of HPBCD: 1.19 mg/mL (150-fold molar excess with respect to molar amount of interferon beta-1a), 3.97 mg/mL (500-fold molar excess with respect to molar amount of interferon beta-1a), 5.56 mg/mL (700-fold molar excess with respect to molar amount if interferon beta-1a) and 7.94 mg/mL (1000-fold molar excess with respect to molar amount of interferon beta-1a). In the Y axis is reported the optical density measured at 360 nm which is directly proportional to turbidimertry (Cancellieri et al, BIOPOLYMERS, VOL 13, 735-743,1974).

The operative conditions used were:
chromatographic column: TSK G2000 $SW_{XL}$ (7.8 mm ID×30 cm, 5 p, 125 Å);
injection volume: 100 μL;
column temperature: room temperature;
sample temperature: room temperature;
flow rate: 0.5 mL/min;
mobile phase: 70% v/v purified water (MILLIQ-Millipore) 30% v/v acetonitrile-0.2% v/v TFA;
run time: 27 min;
equilibration time: 3 min;
wavelength: 214 nm;
A calibration curve, ranged from 25 μg up to 10 μg, was employed to quantify interferon beta-1a assay Materials Interferon beta-1a bulk (Serono S. A., batch G4D024)
PEG 10000 (polyethylenglicole)
Lutrol F68 (polyoxyethilene-polyoxypropilene block copolymer)
L-Methionine
D-Mannitol L-Ascorbic acid
Phosphate Buffer Saline buffer pH 7.4±0.1 (composition: $KH_2PO_4$ 0.19 g/L, $Na_2HPO_4.12H_2O$ 2.38 g/L, NaCl 8 g/L)
Hydroxypropyl-betayclodextrin Equipment
HPLC systems (Waters and PE) equipped with TSK Column.G2000.
UV-visible spectrophotometer system (Perkin Elmer Lambda 40)
Jasco J810 specropolarimeter equipped with a Peltier temperature controller
Osmometer (OSMOMAT 030D, Gonotech)
PH-conductivity Meter MPC 227-Mettler Toledo
Analytical balance AG245 and AG 285 (Mettler Toledo)
Calibrated pipettes (Gilson)
Magnetic stirrer hot plate (Stuart Scientific)
Ultrasonic bath, Falc
Thermometers Results and Discussion Turbidimetry Assay The effect on interferon beta-1a aggregation of HPBCD, mannitol and L-methionine, detected by turbidity method, is reported below. Sodium ascorbate salt is also included as example of excipient having an aggregation-enhancement effect FIG. 1 shows the aggregation kinetic of interferon beta-1a in the presence of different concentrations of HPBCD: 1.19 mg/mL (150-fold molar excess with respect to molar amount of interferon beta-1a), 3.97 mg/mL (500-fold molar excess), 5.56 mg/mL (700-fold molar excess) and 7.94 mg/mL (1,000-molar excess). It can be noticed that in the concentration range investigated this excipient does not avoid completely interferon beta-1a destabilization and that intermediate molar ratios show the best inhibitory effect.

700-fold molar excess was chosen as reference concentration for interferon beta-1a formulation preparation and further physico-chemical characterization (e.g. circular dichroism). The concentration of cyclodextrin is better expressed as molar ratio vs interferon beta-1a (-fold molar excess) as the concentration varies depending on the interferon beta-1a quantity used in the preparation and can be calculated accordingly.

Figure 2:
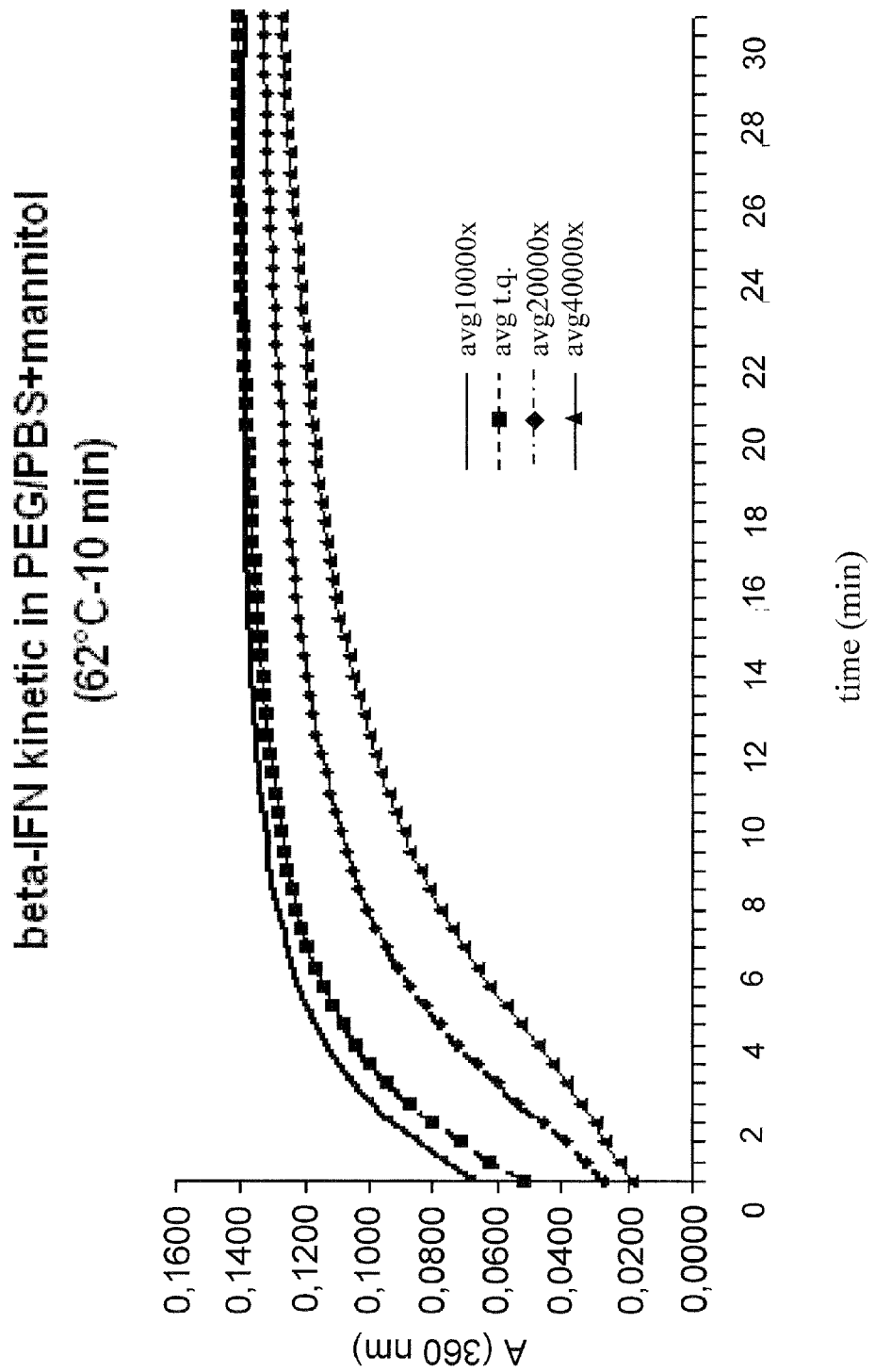
FIG. 2: it shows the effect of 10,000, 20,000 and 40,000 molar excess of mannitol on the aggregation of 0,116 mg/mL (5.1 µM) interferon beta-1a in PBS/PEG10000 (after incubation at 62±3° C. 10 min).

The influence of mannitol on interferon beta-1a aggregation was then monitored but no significant effect was found even at 40,000-fold molar excess (corresponding to 37.35 mg/mL) under the conditions used (62° C. in PEG/PBS), as shown in FIG. 2.

However mannitol was added to interferon beta-1a liquid formulations in order to reach isotonidity necessary for parenteral administration.

Figure 3:
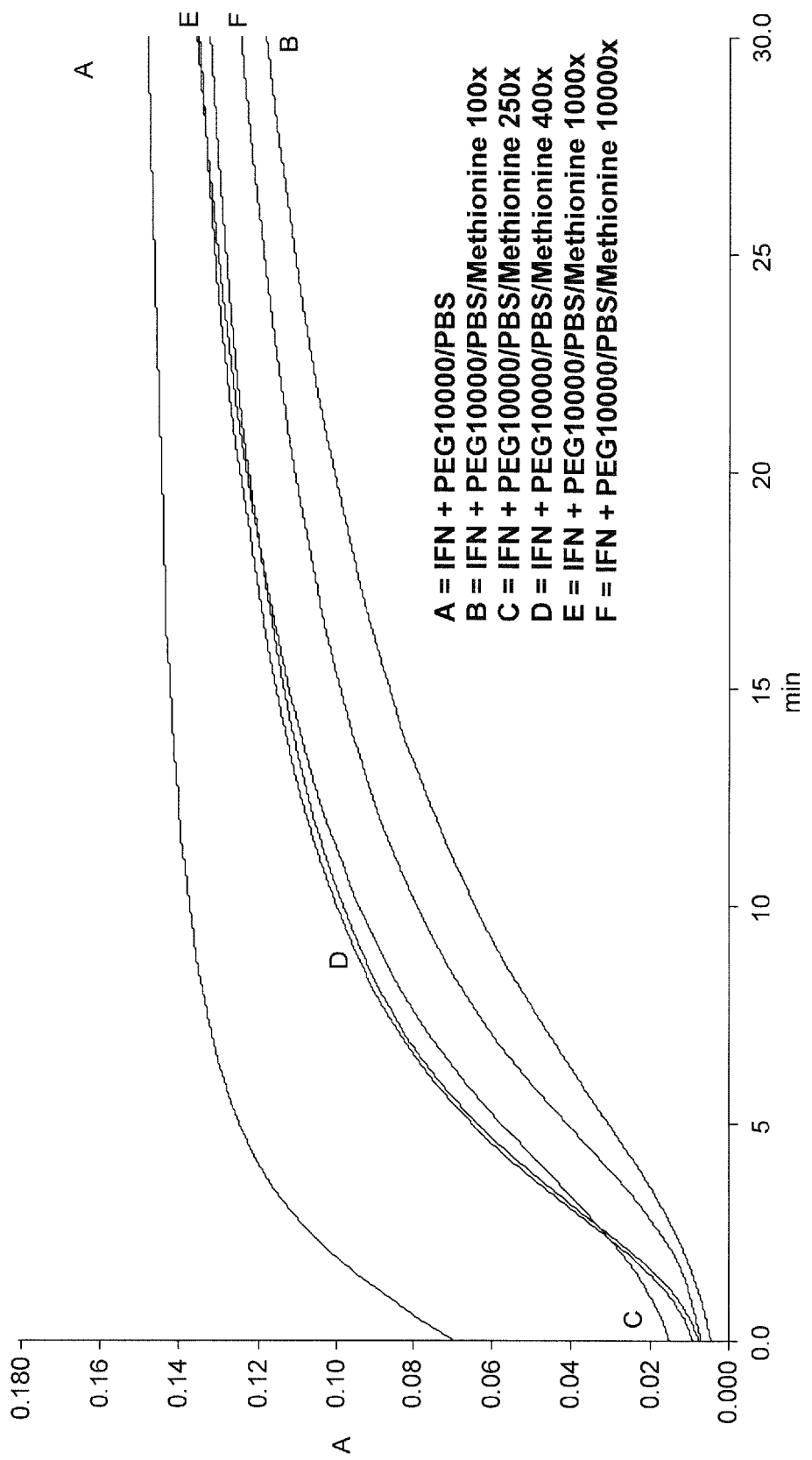
FIG. 3: it shows aggregation kinetic if interferon beta-1a in the presence of different concentrations of L-methionine: 0.077 mg/mL (100-fold molar excess with respect to molar amount of interferon beta-1a), 0.158 mg/mL (205-fold molar excess with respect to molar amount of interferon beta-1a), 0.308 mg/mL (400-fold molar excess with respect to molar amount of interferon beta-1a), 0.769 mg/mL (1000-fold molar excess with respect to molar amount if interferon beta-1a) and 7.69 mg/mL (10000-fold molar excess with respect to molar amount of interferon beta-1a).

Finally, L-Methonine was tested in a turbidimetry experiment. FIG. 3 shows Aggregation kinetic of interferon beta-1a (0.116 mg/mL, in PEG/PBS, after incubation at 62+/−2° C., 10') in the presence of different concentrations of L-methionine.

It can be noticed that L-methionine has a less inhibitory effect on protein aggregation than HPBCD: even at the maximum investigated concentration it does not avoid completely interferon beta-1a destabilization and the curve reaches a "plateau" similar to interferon beta-1a control.

Figure 4:
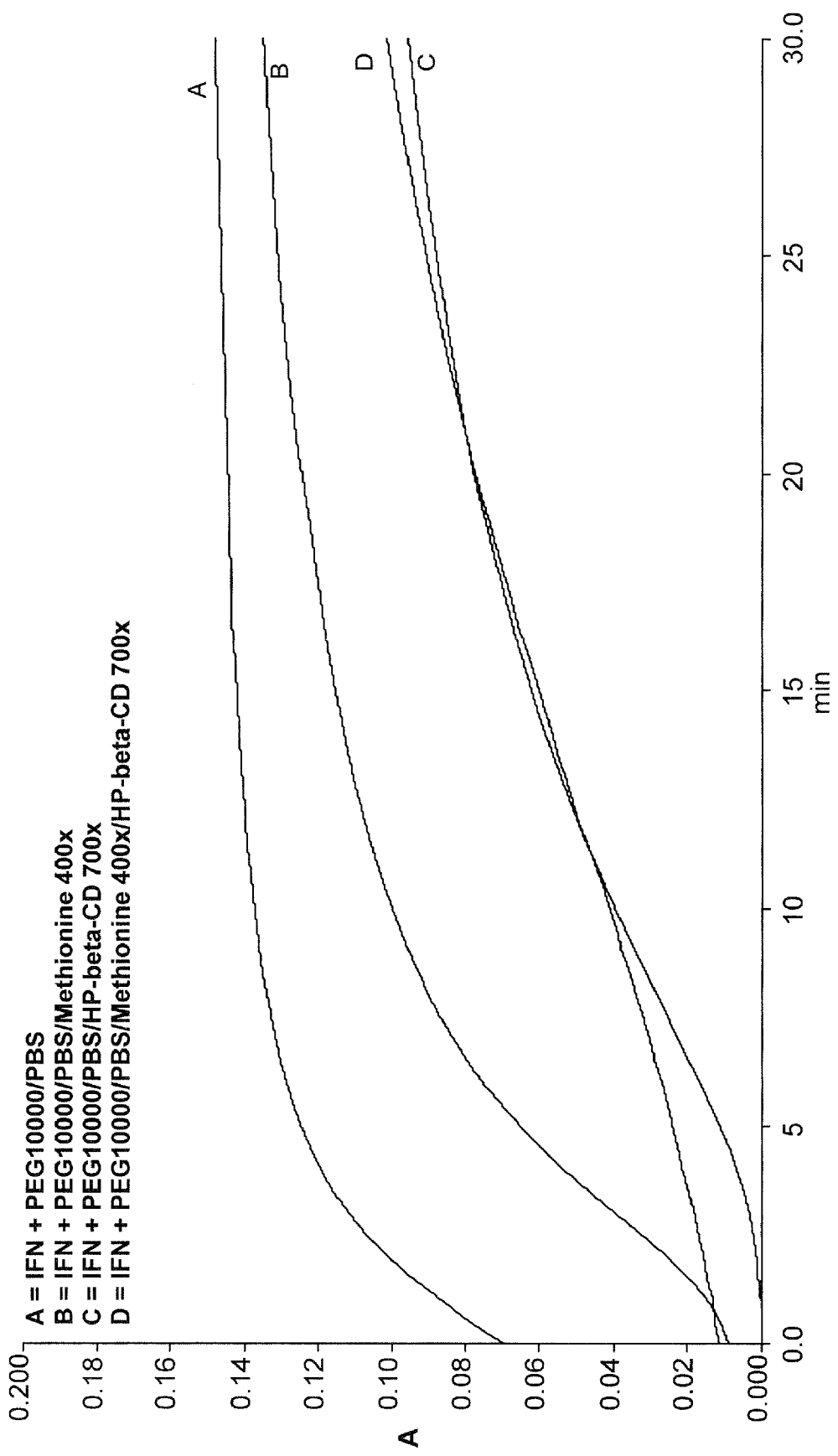
FIG. 4: it shows the aggregation kinetic of interferon beta-1a alone and in the presence of methionine 400-fold molar excess with respect to molar amount of interferon beta-1a (0.308 mg/mL) and/or HPBCD 700-fold molar excess with respect to molar amount of interferon beta-1a (5.56 mg/mL).

In FIG. 4, the aggregation kinetic of interferon beta-1a alone and in the presence of methionine 400-fold molar excess (0.308 mg/mL) and/or HPBCD 700-fold molar excess (5.56 mg/mL) is reported.

This experiment was carried out in order to assess eventually a synergistic effect or interference of these two excipients. It's clear that methionine exerts no protective effect against protein aggregation in addition to the activity of the cyclodextrin.

Following above considerations it was confirmed that the HPBCD was playing a major role in the stabilization of interferon beta-1a toward aggregation and the interaction between the protein and the cyclodextrin was further investigated by circular dichroism.

Figure 5:
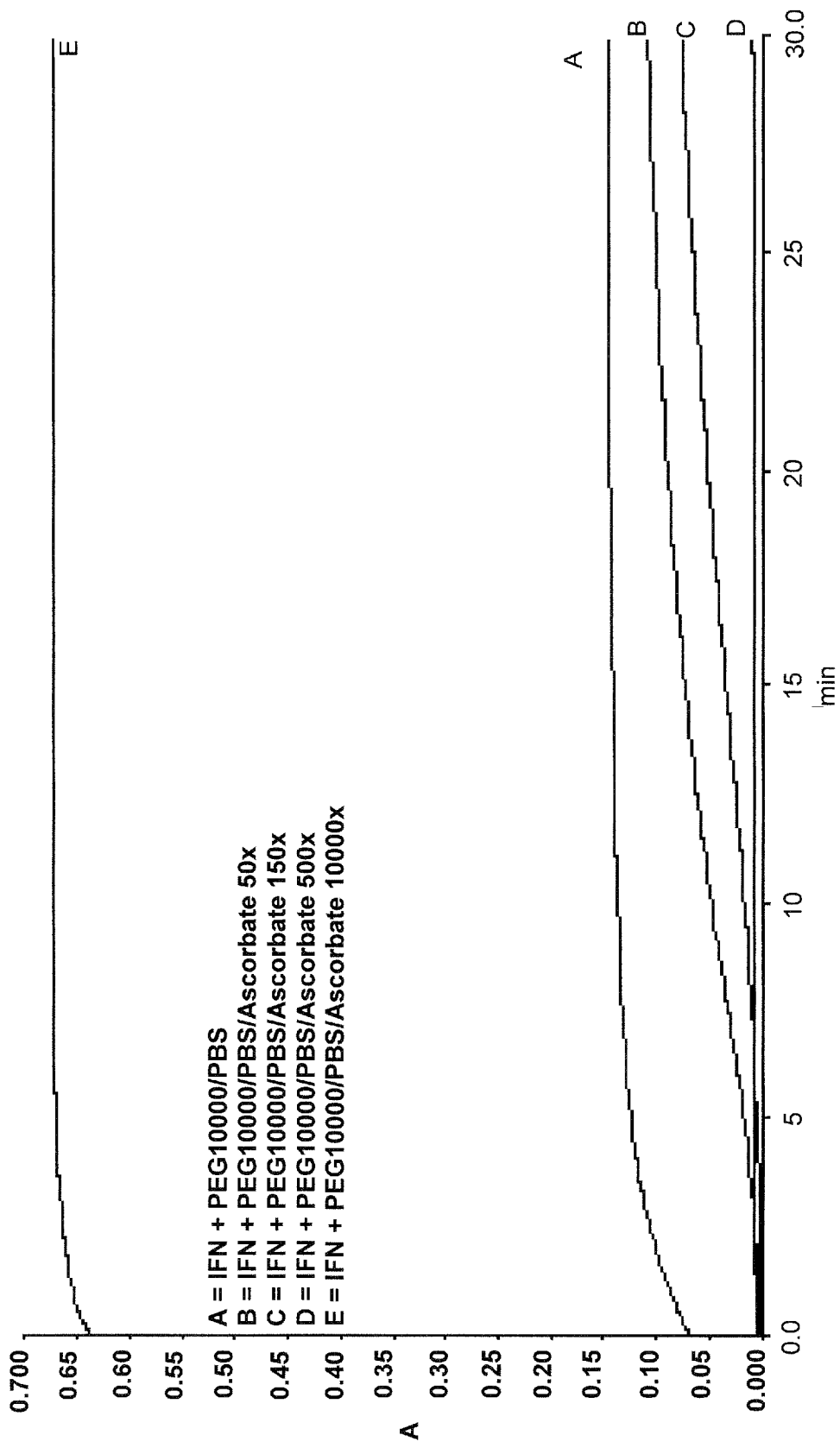
FIG. 5: it shows the effect of L-ascorbate 50-fold molar excess with respect to molar amount of interferon beta-1a (0.045 mg/mL), 150-fold molar excess with respect to molar amount of interferon beta-1a (0.136 mg/mL), 500-fold molar excess with respect to molar amount if interferon beta-1a (0.453 mg/mL) and 10000-fold molar excess with respect to molar amount of interferon beta-1a (9.07 mg/mL) on the aggregation of interferon beta-1a 0.116 mg/mL (5.16 μM) in PEG/PBS, after incubation at 62+/−2° C., 10 minutes.

As example of excipient having "negative effect" on protein aggregation in FIG. 5 the turbidity kinetic of interferon beta-1a in the presence of different concentrations of ascorbate salt is reported.

The effect of L-ascorbate 50-fold molar excess (0.045 mg/mL), 150-fold molar excess (0.136 mg/mL), 500-fold molar excess (0.453 mg/mL) and 10,000-fold molar excess (9.07 mg/mL) on the aggregation of interferon beta-1a 0.116 mg/mL (5.16 µM) in PEG/PBS, after incubation at 62+/−2° C., 10 min. is shown in FIG. 5.

It is interesting to notice that the effect on the protein aggregation varies in a concentration-dependent manner at high concentration negative charges seem to display a destabilizing effect, while at lower molar ratios this excipient seems to have an inhibitory influence.

However it was possible to identify a concentration (0.453 mg/mL corresponding to excipient interferon beta-1a molar ratio equal to 500) that seems to hamper protein aggregation.

The ascorbate was then chosen as possible excipient for interferon beta-1a formulations, with the purpose of combining its antioxidant action with a specific anti-aggregation effect.

Circular Dichroism

Figure 6:
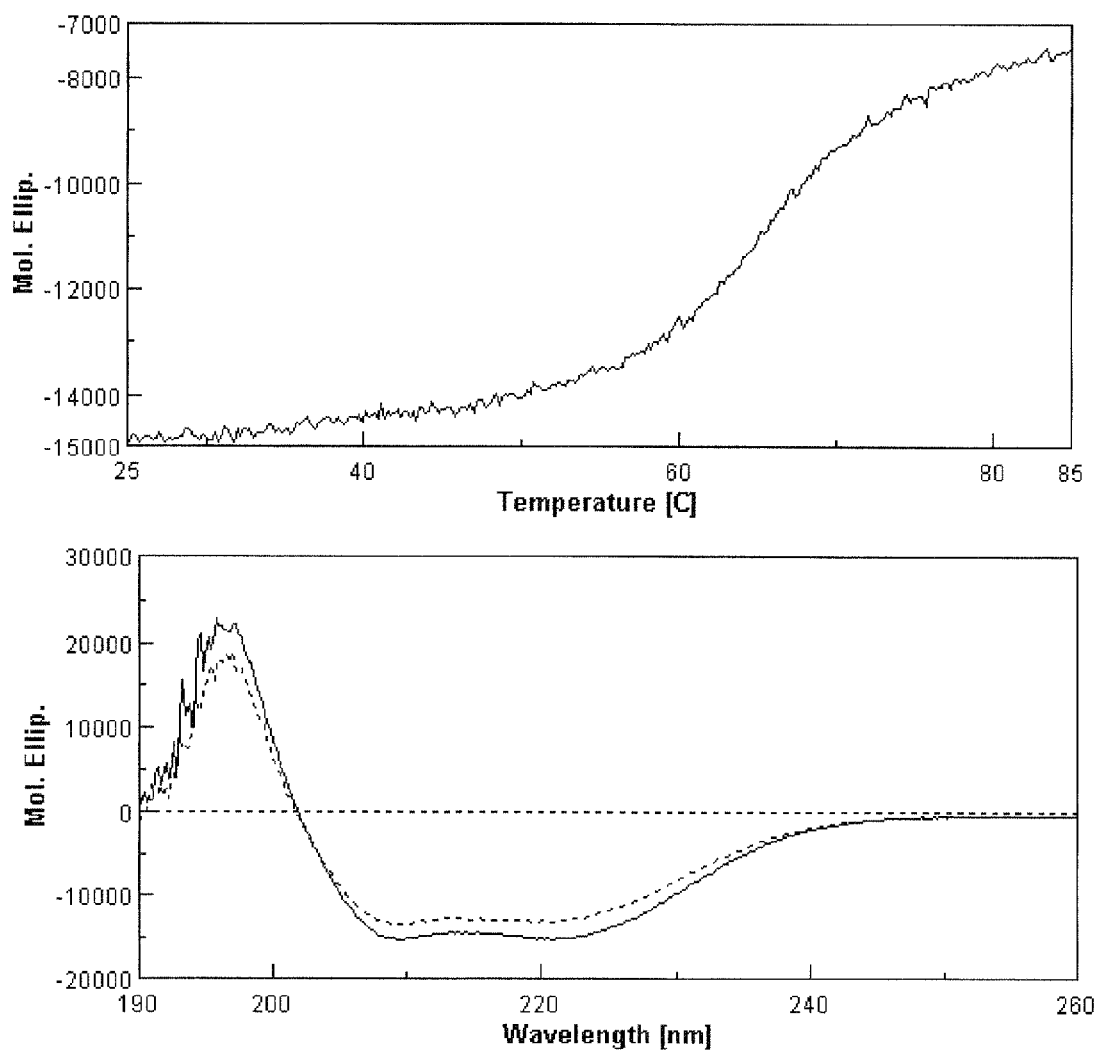
FIG. 6: it reports the interferon beta-1a bulk (about 44 μg/mL) thermal denaturation (i.e. effect of temperature on CD signal at 222 nm) in the upper part of the figure and the relative CD spectrum before (solid line) and after (dash line) malting transition in the lower part of the figure. Hereinafter the respective CDNN (Circular Dichroism Neural Network) deconvolutions (average of four analyses) are reported. N.B.: The melting transition curve or thermal denaturation represents the effect of temperature on CD signal at 222 nm. All CD graphs have in Y-axis the molar ellipticity as deg $M^{-1}$ $cm^{-1}$ (Y axis)

In FIG. 6 thermally induced unfolding, between 25° C. and 85° C., and far-UV spectra of interferon beta-1a bulk sample (about 44 µg/mL) are reported. It can be noticed that the estimated $T_m$ value is 64.97±0.31° C., while spectrum deconvolution shows a remarkable difference in the α-helix content pre- and post-denaturation, such as respectively 48.0 vs 41.2%.

As a comparison an analogous sample containing hydroxypropyl-beta-cyclodextrin was analysed by circular dichroism at 700-fold molar excess with respect to the molar amount of interferon beta-1a, being the concentration where protein aggregation is partially inhibited in the turbidimetry experiment. In FIG. 7 thermal denaturation curve is reported for a solution containing interferon beta-1a about 44 µg/mL and HPBCD 2.11 mg/mL (700 molar excess). The estimated melting temperature value was 65.46±0.50° C., identical to that one (64.97° C.) concerning protein alone in the same operative conditions (see FIG. 5).

Although the melting temperature of the protein is constant in the presence of the tested additive, the reversibility of thermal unfolding is very different. It can be noticed that in the presence of HPBCD there is clearly a smaller interferon beta-1a α-helix gap between pre- and post-denaturation situation (about 4% difference versus about 7% for the protein alone), suggesting that the cyclodextrin might prevent interferon beta-1a irreversible reactions, such as heat-induced aggregation following unfolding, or assist the refolding of the protein. These observations are very interesting because finding formulation compositions that make unfolding reversible may be actually more important for long-term stability (shelf life) than raising the melting temperature (see also Arakawa et al, in *Adv. Drug Deliv. Rev.* 46(1-3):307-326 (2001)).

In order to better characterize the interaction of interferon beta-1a with sodium ascorbate salt a CD analysis was performed on an interferon beta-1a sample containing 500-fold molar excess of ascorbate salt. Indeed kinetic turbidity studies revealed that an ascorbate-interferon beta-1a solution, at molar ratio equal to 500, display no protein aggregation.

In FIG. 8 the effect of temperature on the CD signal (222 nm) of interferon beta-1a (about 44 µg/mL) alone and in presence of 500-fold molar excess of ascorbate (0.194 mg/mL) are shown. In the case of the sample containing ascorbate it was not possible to fit the experimental curve in order to estimate $T_m$ value, suggesting a denaturing effect of the excipient toward the protein.

Indeed the comparison of the secondary structure of the sample above, before and after the melting transition confirmed a very low residual of alpha-helix already in the pre-melting situation, such as 35.0 (vs 48.0 of interferon beta-1a bulk in the same conditions). Interferon beta-1a secondary structure was even more altered by the presence of the ascorbate after the melting transition, decreasing down to 28.8% (see FIG. 9).

This result is in contrast with the protective effect shown in turbidimetry and suggests that ascorbate might-induce interferon beta-1a confomational changes that could destabilize the protein upon time. For this reason a liquid formulation containing sodium ascorbate was prepared, kept in stability at 25° C. and analysed at pre-fixed timepoints by SE-HPLC.

Stability Study

Following above results, two interferon beta-1a liquid formulations, having the compositions shown in Tab.1 and Tab.2, were prepared and kept at 25° C. and 50° C. over time in the case of FORM 1 and at 25° C. in the case of FORM2.

As a control, interferon beta-1a bulk (50 mM in acetate buffer at same concentration) was also tested.

TABLE 1

Composition of Interferon beta-1a liquid formulation containing HPBCD (FORM1).

| | |
|---|---|
| Interferon beta-1a | 44 µg/mL |
| HPBCD | 1.9 mg/mL |
| Methionine | 0.1 mg/mL |
| Mannitol | 50 mg/mL |
| acetate buffer (50 mM; pH = 3.8) up to | 1 mL |

TABLE 2

Composition of Interferon beta-1a liquid formulation containing sodium ascorbate (FORM2)

| | |
|---|---|
| Interferon beta-1a | 44 µg/mL |
| Sodium ascorbate | 0.2 mg/mL |
| Lutrol F68 | 0.8 mg/mL |
| Mannitol | 50 mg/mL |
| acetate buffer (50 mM; pH = 3.8) up to | up to 1 mL |

The samples from the stability study were analysed by SE-HPLC as described in Method section and the results are reported in Table 3 (FORM1), Table 4 (FORM2) and Table 5 (interferon beta-1a Bulk/Control).

TABLE 3

SE-HPLC results of stability study on FORM1 formulation at 25° C. and 50° C.
FORM1

| Time | visual inspection | purity % area by HPLC | assay recovery % (W/W) |
|---|---|---|---|
| T = 0 | clear | 96.96 | 102.9 |
| t = 1 week/25° C. | clear | 96.86 | 100.29 |
| t = 1 month/25° C. | clear | 97.06 | 100.43 |
| t = 0 | Clear | 96.96 | 102.9 |
| t = 24 h/50° C. | Clear | 97.5 | 99.29 |
| t = 48 h/50° C. | Clear | 97.3 | 98.79 |
| t = 1 week/50° C. | Clear | 95.63 | 94.31 |

TABLE 4

SE-HPLC results of stability study on FORM2 formulation at 25° C.
FORM2

| Time | visual inspection | purity % area by HPLC | assay recovery % (W/W) |
|---|---|---|---|
| T = 0 | clear | 97.49 | 116.2 |
| t = 24 h | clear | NA | NA |
| t = 1 week 25° C. | clear | 97.84 | 70.27 |
| t = 1 month 25° C. | clear | 60.305* | 36.54 |

*degradation peak with rrt: 1.13: area %5.37

TABLE 5

SE-HPLC results of stability study on Interferon beta-1a control formulation at 25° C. and 50° C.
Interferon beta-1a BULK

| Time | visual inspection | purity % area by HPLC | Assay recovery % (W/W) |
|---|---|---|---|
| t = 0 | clear | 97.95 | 102.7 |
| t = 24 h/25° C. | clear | N/A | N/A |
| t = 1 week/25° C. | clear | 97.41 | 95.73 |
| t = 1 month 25° C. | clear | 97.65 | 93.12 |
| t = 24 h/50° C. | clear | 93.84 | 95.90 |
| t = 48 h/50° C. | clear | 91.19 | 94.60 |
| t = 72 h/50° C. | clear | 89.25 | 91.69 |
| t = 1 week/50° C. | clear | 83.42 | 73.26 |

From results in Table 3 it can be clearly seen that interferon beta-1a liquid formulation containing HPBCD are stable at 25° C. and 50° C. over 1 month: the aggregation level is very low, being the monomer content above 90% even after 1 week at 50° C. In addition the mass recovery is above 90% suggesting that also the formation of insoluble aggregates might be minimized by the presence of the cyclodextrin.

In comparison the interferon beta-1a bulk alone tends to aggregate at both considered temperatures (see Table 5): at 50° C. after 1 week the monomer content decreased down to 83% and in parallel the mass recovery was only about 73%.

The latter results are in agreement with the turbidimetry and circular dichroism measurements that have suggested a beneficial effect of HPBCD on interferon beta-1a aggregation and conformational stability.

Finally, the results shown in Table 4 related to FORM2 (containing ascorbate salt) indicate that the formulation is not stable at 25° C.: a significant increase of dimers and aggregates and a parallel decrease of mass recovery were recorded after 1 month at 25°. Furthermore an unknown peak appeared in the chromatogram suggesting the presence of possibly changed conformation, as suggested also by CD results. This was the reason why the stability of the formulation containing ascorbate was not performed at higher temperatures (e.g. 50° C.).

In the latter case it was important to verify the initial promising result obtained by turbidimetry analysis with alternative methods such as circular dichroism that is able to monitor the effect of a known excipient on the protein conformation stability.

Turbidimetry Assay at Higher pH

The effect on interferon beta-1a aggregation of HPBCD in a wider pH range of the liquid formulation (i.e. pH about 3.0 to about 4-0) was investigated.

The method consisted in the previously described turbidimetric assay: interferon beta-1a bulk was diluted 12 with a solution of PEG 10,000 30 mg/mL in PBS (0-2 μm Ø filtered and properly basified by adding a small volume of NaOH 1N) and then incubated in a thermostatic water bath at T=62±2° C. for 10 min. Protein aggregation was monitored for 30 min at 360 nm using an UV-visible spectrophotometer system (Perkin Elmer Lambda 40). Each turbidity analysis was repeated in duplicate and the optical density $(OD)_{380\ min}$ versus time average curve is reported. Aggregation of the protein alone was compared to interferon beta-1 a in the presence of cyclodextrin.

The dilution of acetate buffer 50 mM (i.e. IFN bulk medium) 1:1 by PBS leads to a final solution pH of 4.4. The aim was therefore to investigate protein aggregation for higher final pH.

FIG. 10 shows the aggregation kinetic of interferon beta-1a in the absence and in the presence of a 700× M excess of HPBCD (5.56 mg/mL), with a pH of the analysed solution equal to 4.7 at room temperature.

It can be noticed that an increment of pH enhances the extent of IFN aggregation, but the presence of cyclodextrin still partially inhibits protein destabilization. The relative percentage OD (i.e. percentage ratio between OD 96 nm after 30 min in the presence and in the absence of the excipient) calculated for this experiment is 66%, not so far from what observed in the usual operative conditions at lower pH (52.7%).

The study was extended to a higher pH. i.e. 5.1, as shown in FIG. 11: the effect of HPBCD at a 700 M excess (5.56 mg/mL) and of RMBCD at a 500 M excess (3.38 mg/mL) on IFN aggregation was investigated. It can be noticed a more marked protein destabilization due to the increase of pH and the almost total absence of a kinetic trend (i.e. plateau region at the beginning of the analysis). The interesting finding is that IFN aggregation is still partially inhibited by cyclodextrins, with a relative percentage OD equal to 69.7% in the case of HPBCD (no advantage can be observed by the use of the methyl-derivative in this case).

A third pH value was investigated. FIG. 12 shows IFN aggregation kinetic in PEG/PBS at pH 5.7 and the effect of addition of a 700× molar excess of HPBCD. The excipient does not avoid protein destabilization, but significantly reduces its extent with respect to IFN control (relative percentage OD 62.5%).

The above considerations indicate that the use of HPBCD as stabilizing excipient could be extended to liquid formulation at pH higher than the protein bulk characteristic value (i.e. pH 3.8±0.5).

Conclusions

Some interferon beta-1a liquid formulations were prepared and kept in stability at room temperature (25° C.) and in accelerated conditions (50° C.).

The most stable formulation contains L-methionine, HPBCD and mannitol. SE-HPLC results show a monomer content above 90% after 1 week at 50° C. or 1 month at 25° C.

The positive result of HPBCD was anticipated and confirmed by turbidimetry measurement that showed a concentration dependent-inhibition effect of this excipient, (and partially also of L-methionine), toward interferon beta-1a aggregation. Furthermore CD analysis showed that in the presence of HP-beta-cyclodextrin there is clearly a smaller interferon beta-1a a-helix loss after melting transition.

The interferon beta-1a bulk, kept in the same storage conditions, displays a different stability profile; the monomer content decreased down to 83% after 1 week at 50° C.

Of note at 25° C. the monomer content after 1 month is still equal to 97%, which is surprisingly high. This result could be explained by the fact that the bulk contains acetate buffer at pH 3.8. This condition has itself a certain degree of stabilizing effect for interferon beta-1a.

A clear negative result in the stability study was found with the formulation containing ascorbate salt SEC shows a remarkable monomer loss (down to 60%) at 25° C. after 1 month. In parallel a negative effect on interferon beta-1a conformation was also shown by CD analysis.

Pharmaceutical Manufacturing

Preparation of Sodium Hydroxide 1M Solution

A solution of 1 M sodium hydroxide was prepared in WFI.

Preparation of 0.05 M Sodium Acetate Buffer pH 3.8 (100 mL)

In a volumetric flask containing 80 mL of MilliQ water add 0.286 mL of acetic acid (Glacial), and, after shaking, add 0.500 mL of NaOH 1M and water up to 100 mL; pH=3.8±0.05.

Preparation of the Excipient Solution

A concentrated (10-fold) solution of HPBCD and L-Methionine in acetate buffer is prepared in polypropylene volumetric flask.

In the polypropilene flask the suitable amount of acetate buffer 50 mM containing 5 g of mannitol is added. The solution is brought to homogeneity by turning up and down three times.

Compounding of the Drug Substance Solution

The required amount B(g) if interferon beta-1a drug substance is added to the required amount of excipient solution V(g) and gently stirred to homogeneity.

Filling of Syringes 1 ml glass syringes may be aseptically filled with 0.5 ml of the final solution.

REFERENCES

1. Arakawa, Prestrelski, Kenney and Carpenter (2001), "Factors affecting short-term and long-term stabilities of proteins", Adv. Drug Deliv. Rev. 46(1-3):307-326;
2. Brewster et al., 1991, Pharmaceutical research, New York, 8(6), 792-795;
3. Cancellieri et al., Biopolymers, VOL 13, 735-743, 1974;
4. Clegg and Bryant, Exp. Opin. Parmacother 2001; 2(4): 623-639;
5. Derynk R. et al., Nature 1980; 285, 542-547;
6. Familletti, P. C., Rubinstein, S., and Pestka, S. 1981 "A Convenient and Rapid Cytopathic Effect Inhibition Assay for Interferon," In Methods In Enzymology, Vol. 78 (S. Pestka, ed.), Academic Press, New York, 387-394;
7. Hultgren C, Milich D R, Weiland O, Sallberg M. (1998). The antiviral compound ribavirin modulates the T helper (Th) 1/Th2 subset balance in hepatitis B and C virus-specific immune responses. J Gen Virol 1998; 79:2381-2391;
8. T. Irie et al., 1999, Adv. Drug Deliv. Rev, Vol 36, 101-123;
9. McCormick J B, King I J, Webb P A, Scribner C L, Craven R B, Johnson K M, Elliott L H, Belmont-Williams R. Lassa fever. Effective therapy with ribavirin. N Engl J Med. 1986 Jan. 2; 314(1):20-6;
10. Mark D. F. et al., Proc. Natl. Acad. Sci. U.S.A., 81 (18) 5662-5666 (1984);
11. Pagington, Chemistry in Britain, pp. 455-458 (1987);
12. Pestka, S. (1986) "Interferon Standards and General Abbreviations, in Methods In Enzymology (S. Pestka, ed.), Academic Press, New York 119, 14-23;
13. Pitha et al, International Journal of Pharmaceutics, 29, 73-82 (1986);
14. Pitha et al, in Controlled Drug Deliver, ed. S. D. Bruck, Vol. 1, CRC Press, Boca Raton, Fla., pp. 125-148 (1983);
15. Rubinstein, S., Familletti, P. C., and Pestka, S. Convenient Assay for Interferons. J. Virol 1981; 37, 755-758;
16. Shepard H. M. et al., Nature 1981; 294, 563-565;
17. T. Irie et al., Cyclodextrins in peptide and protein delivery, Adv. Drug Deliv. Rev, Vol 36, 101-123 (1999);
18. Study Group. The Lancet 1998; 352, 1498-1504;
19. Uekama et al, In CRC Critical Reviews In Therapeutic Drug Carrier Systems, Vol. 3 (1), 140 (1987);
20. Uekama, in Topics in Pharmaceutical Sciences 1987, eds. Breimer and Speiser, Elsevier Science Publishers B. V. (Biomedical Division), 181-194 (1987);
21. Wang et al., Int. J. Pharm, 185:129-188;
22. Wang et a., J. Parenteral Sci. Tech., 1998, 42:S3-S26;
23. WO 03 00/2152;
24. WO 99/55377;
25. WO 90/03784;
26. U.S. Pat. No. 6,582,728;
27. U.S. Pat. No. 6,013,253;
28. U.S. Pat. No. 5,997,856;
29. U.S. Pat. No. 5,541,293;
30. U.S. Pat. No. 5,116,943;
31. U.S. Pat. No. 5,017,691;
32. U.S. Pat. No. 4,965,195;
33. U.S. Pat. No. 4,959,314;
34. U.S. Pat. No. 4,904,584;
35. U.S. Pat. No. 4,897,471;
36. U.S. Pat. No. 4,879,111;
37. U.S. Pat. No. 4,737,462;
38. U.S. Pat. No. 4,695,623;
39. U.S. Pat. No. 4,588,585.

The invention claimed is:

1. A stabilized liquid pharmaceutical composition comprising an interferon (IFN) or salt thereof, a buffer, 2-hydroxypropyl-beta-cyclodextrin ("HPBCD"), an isotonicity agent and an anti-oxidant, wherein said HPBCD is present at about a 500-fold to about a 700-fold molar excess with respect to said interferon.

2. The composition according to claim 1, wherein said interferon is IFN-beta.

3. The composition according to claim 2, wherein said IFN-beta is recombinant human IFN-beta.

4. The composition according to claim 1, wherein said buffer is present in an amount sufficient to maintain the pH of said composition within plus or minus 0.5 units of a specified pH, where the specified pH is about 3 to about 6.

5. The composition according to claim 4, wherein said pH is 3.8.

6. The composition according to claim 1, wherein said buffer is present at a concentration of about 5 mM to 500 mM.

7. The composition according to claim 6, wherein said buffer is present at a concentration of about 50 mM.

8. The composition according to claim 1, wherein the buffer is acetate buffer.

9. The composition according to claim 1, wherein said isotonicity agent is mannitol.

10. The composition according to claim 1, wherein said isotonicity agent is present at a concentration of about 0.5 mg/ml to about 500 mg/ml.

11. The composition according to claim 10, wherein said isotonicity agent is present at a concentration of about 50 mg/ml.

12. The composition according to claim 1, wherein said antioxidant is methionine.

13. The composition according to claim 1, wherein said antioxidant is present at a concentration of about 0.01 to about 5 mg/ml.

14. The composition according to claim 13, wherein said antioxidant is present at a concentration of about 0.1 mg/ml.

15. The composition according to claim 1, wherein said interferon is present at a concentration of about 10 µg/ml to about 800 µg/ml.

16. The composition according to claim 1, wherein said interferon is present at a concentration of about 44 µg/ml.

17. The composition according to claim 1, wherein said interferon is present at a concentration of about 88 µg/ml.

18. The composition according to claim 1, wherein said interferon is present at a concentration of about 276 µg/ml.

19. The composition according to claim 1, wherein said composition is an aqueous solution.

20. The composition according to claim 1, further comprising a bacteriostatic agent.

21. The composition according to claim 20, wherein said bacteriostatic agent is benzyl alcohol.

22. The composition according to claim 20, wherein said bacteriostatic agent is present at a concentration of about 0.1% to about 2%.

23. The composition according to claim 20, wherein said bacteriostatic agent is present at a concentration of about 0.2 or 0.3%.

24. The composition according to claim 1, wherein the isotonicity agent is mannitol, the anti-oxidant is methionine and the interferon is interferon beta.

25. An article of manufacture comprising the composition of claim 1 in a container.

26. An article of manufacture comprising a container containing a stabilized liquid pharmaceutical composition comprising:
  (a) an interferon (IFN) or a salt thereof, wherein said composition is a solution that comprises a buffer, 2-hydroxypropyl-beta-cyclodextrin, an isotonicity agent and an anti-oxidant, wherein said cyclodextrin is present at a molar ratio vs. interferon of from 500-fold molar excess up to 700-fold molar excess; or
  (b) a composition comprising an interferon (IFN) or a salt thereof, wherein said composition is a solution that comprises a buffer, 2-hydroxypropyl-beta-cyclodextrin, an isotonicity agent and an anti-oxidant, wherein said composition comprises the following components in an acetate buffer:

| Interferon-beta-1a | 44 | µg/mL |
| --- | --- | --- |
| HPBCD | 1.9 | mg/mL |
| Methionine | 0.1 | mg/mL |
| Mannitol | 50 | mg/mL; | and wherein said container is hermetically sealed in conditions that are sterile and appropriate for storage prior to use.

27. The article of manufacture according to claim 26, wherein said container is for mono-dose administration.

28. The article of manufacture according to claim 27, wherein said container is a pre-filled syringe for mono-dose administration.

29. The article of manufacture according to claim 27, wherein said container is a vial.

30. The article of manufacture according to claim 27, wherein said container is a cartridge for an auto-injector.

31. The article of manufacture according to claim 26, wherein said article of manufacture is a kit for multi-dose administration of a pharmaceutical composition, said kit comprising a first container, said first container comprising a container containing said stabilized liquid pharmaceutical composition and a second container filled with a solution of a bacteriostatic agent.

32. The article of manufacture according to claim 26, wherein said container is for multidose administration.

33. A composition comprising the following components in an acetate buffer:

| Interferon beta-1a | 44 µg/mL |
| --- | --- |
| HPBCD | 1.9 mg/mL |
| Methionine | 0.1 mg/mL |
| Mannitol | 50 mg/mL. |

34. The composition according to claim 33, wherein the composition consists of the following components in an acetate buffer:

| Interferon beta-1a | 44 µg/mL |
| --- | --- |
| HPBCD | 1.9 mg/mL |
| Methionine | 0.1 mg/mL |
| Mannitol | 50 mg/mL. |

35. An article of manufacture comprising the composition of claim 34 in a container.

* * * * *

UNITED STATES PATENT AND TRADEMARK OFFICE
CERTIFICATE OF CORRECTION

| | |
|---|---|
| PATENT NO. | : 7,846,427 B2 |
| APPLICATION NO. | : 10/582027 |
| DATED | : December 7, 2010 |
| INVENTOR(S) | : Maria Dorly Del Curto |

It is certified that error appears in the above-identified patent and that said Letters Patent is hereby corrected as shown below:

Column 1,
Line 60, "Burkit's lymphoma" should read --Burkitt's lymphoma--.

Column 2,
Line 10, "There is a duster" should read --There is a cluster--.
Line 19, "agents can are sometimes" should read --agents are sometimes--.
Lines 29-30, "166 amino acid" should read --166 amino acids--.

Column 3,
Line 4, "cydodextrins are" should read --cyclodextrins are--.
Line 18, "(2,6-dimethyl)-beta-cyclodextrin" should read
    --(2,6-di-O-methyl)-beta-cyclodextrin--.
Line 31, "has bee" should read --has been--.
Line 32, "T. Ide" should read --T. Irie--.
Line 40, "stabilization if" should read --stabilization of--.

Column 4,
Line 2, "hum an serum" should read --human serum--.
Line 58, "polynucleotide's" should read --polynucleotides--.

Column 5,
Line 7, "amino adds" should read --amino acids--.
Line 14, "amino add" should read --amino acid--.

Column 7,
Line 65, "sulfuric add, and salts with organic adds" should read
    --sulfuric acid, and salts with organic acids--.
Line 66, "oxalic add" should read --oxalic acid--.

Signed and Sealed this
First Day of March, 2011

David J. Kappos
*Director of the United States Patent and Trademark Office*

CERTIFICATE OF CORRECTION (continued)
U.S. Pat. No. 7,846,427 B2

Column 8,
Line 7, "so called" should read --so-called--.
Line 23, "amino add" should read --amino acid--.
Line 32, "tripe tide" should read --tripetide--.
Line 43, "an IgG$_2$, molecule." should read --an Ig molecule.--.
Lines 64-65, "80 000 IU/kg and 200 000" should read --80,000 IU/kg and 200,000--.

Column 9,
Line 9, "one, twice" should read --once, twice--.
Line 15, "IFN-β In the" should read --IFN-β in the--.

Column 10,
Lines 42-43, "hydroxypropyl-gaamma-cyclodextrin" should read
    --hydroxypropyl-gamma-cyclodextrin--.
Line 45, "or GlBCD)" should read --or G$_1$BCD)--.
Line 50, "maltotriosylgamma-cyclodextrin" should read
    --maltotriosyl-gamma-cyclodextrin--.
Lines 52-53, "maltosyl-beta-cydodextrin/dimaltosyl-beta-dodextrin" should read
    --maltosyl-beta-cyclodextrin/dimaltosyl-beta-cyclodextrin--.

Column 11,
Line 21, "bacterostatic" should read --bacteriostatic--.
Line 26, "product Examples" should read --product. Examples--.

Column 13,
Line 4, "IFN beta" should read --IFN-beta--.
Line 14, "in the are buffer" should read --in the art. Buffer--.

Column 15,
Line 40, "the invention include" should read --the invention includes--.

Column 16,
Line 53, "amount if" should read --amount of--.
Line 65, "amount if" should read --amount of--.

Column 17,
Line 7, "malting" should read --melting--.
Line 46, "and 5(0x M" should read --and 500x M--.

Column 18,
Line 48, "5 p" should read --5 μ--.
Line 59, "up to 10 μg" should read -- up to 100μg--.

Column 19,
Line 5, "Hydroxypropyl-betayclodextrin" should read
--Hydroxypropyl-beta-cyclodextrin--.
Line 56, "isotonidity" should read --isotonicity--.

Column 20,
Line 26, "manner at" should read --manner: at--.
Line 31, "excipient interferon" should read --excipient/interferon--.

Column 23,
Line 12, "about 4-0)" should read --about 4.0)--.
Line 14, "diluted 12" should read --diluted 1:2--.
Line 21, "$(OD)_{380\ min}$" should read --$(OD)_{360nm}$--.
Line 36, "OD 96 nm" should read --$OD_{360\ nm}$--.

Column 24,
Line 11, "a-helix" should read --α-helix--.

Column 25,
Line 8, "8. T. Irie" should read --8. Irie--.
Line 59, "140 (1987)" should read --1-40 (1987)--.
Line 64, "22. Wang et a." should read --22. Wang et al.--.